(12) United States Patent
Peterson et al.

(10) Patent No.: US 8,074,857 B2
(45) Date of Patent: Dec. 13, 2011

(54) METHOD AND APPARATUS FOR TISSUE FASTENING WITH SINGLE TRANSLATING TRIGGER OPERATION

(75) Inventors: James A. Peterson, Edina, MN (US); Christopher J. Sperry, Plymouth, MN (US); Joseph M. Gryskiewicz, Edina, MN (US); Delmer L. Smith, Edina, MN (US); David B. Herridge, Mendota Heights, MN (US)

(73) Assignee: Incisive Surgical, Inc., Plymouth, MN (US)

( * ) Notice: Subject to any disclaimer, the term of this patent is extended or adjusted under 35 U.S.C. 154(b) by 1247 days.

(21) Appl. No.: 11/022,319

(22) Filed: Dec. 23, 2004

(65) Prior Publication Data

US 2005/0149064 A1 Jul. 7, 2005

Related U.S. Application Data

(60) Continuation-in-part of application No. 10/448,838, filed on May 30, 2003, now Pat. No. 7,686,200, which is a division of application No. 10/179,628, filed on Jun. 25, 2002, now Pat. No. 6,726,705, application No. 11/022,319, which is a continuation-in-part of application No. 10/607,497, filed on Jun. 25, 2003, now Pat. No. 7,950,559, and a continuation-in-part of application No. 10/603,397, filed on Jun. 25, 2003, now Pat. No. 7,112,214.

(51) Int. Cl.
*A61B 17/10* (2006.01)
(52) U.S. Cl. ............ 227/175.1; 606/142; 606/219
(58) Field of Classification Search .......... 606/142, 606/219, 216, 143; 227/175.1, 176.1
See application file for complete search history.

(56) References Cited

U.S. PATENT DOCUMENTS 2,283,814 A 5/1942 La Place
(Continued)

FOREIGN PATENT DOCUMENTS

EP 1 323 384 A2 7/2003
(Continued)

OTHER PUBLICATIONS

Brochure: *Information Booklet for Auto Suture® Purse String Instrument*, Auto Suture Company, a division of United States Surgical Corporation, Norwalk, CT, 2 pgs., 1978.
(Continued)

*Primary Examiner* — Gary Jackson
*Assistant Examiner* — Michael Mendoza
(74) *Attorney, Agent, or Firm* — Patterson Thuente Christensen Pedersen, P.A.

(57) ABSTRACT

A mechanical device and method for gathering and securing tissue with a fastener. The device includes an applicator assembly configured to deploy a fastener in a first direction, a tissue manipulation assembly configured to move from a relaxed position to a grasping position in a second direction transverse to the first direction, and a translating trigger assembly coupled to the applicator assembly and the tissue manipulation assembly. The trigger assembly is configured to move from a relaxed position, through a first position, to a second position along a third direction transverse to the first and second direction. Operation of the trigger assembly from the relaxed position through the first position along the third direction causes the tissue manipulation assembly to move in the second direction to gather a portion of the tissue. Continued operation of the trigger assembly along the third direction causes the applicator assembly to deploy the fastener.

19 Claims, 20 Drawing Sheets

U.S. PATENT DOCUMENTS

| | | |
|---|---|---|
| 2,351,608 A | 6/1944 | Greenwood |
| 2,439,383 A | 4/1948 | Erickson |
| 2,526,902 A | 10/1950 | Rublee |
| 2,881,762 A | 4/1959 | Lowrie |
| 2,959,172 A | 11/1960 | Held |
| 3,082,426 A | 3/1963 | Miles |
| 3,123,077 A | 3/1964 | Alcamo |
| 3,297,033 A | 1/1967 | Schmitt et al. |
| 3,344,790 A | 10/1967 | Dorner |
| 3,636,956 A | 1/1972 | Schneider |
| 3,643,851 A | 2/1972 | Green et al. |
| 3,716,058 A | 2/1973 | Tanner, Jr. |
| 3,757,629 A | 9/1973 | Schneider |
| 3,792,010 A | 2/1974 | Wasserman et al. |
| 4,014,492 A | 3/1977 | Rothfuss |
| 4,027,676 A | 6/1977 | Mattei |
| 4,047,533 A | 9/1977 | Perciaccante et al. |
| 4,162,678 A | 7/1979 | Fedotov et al. |
| 4,164,225 A | 8/1979 | Johnson et al. |
| 4,259,959 A | 4/1981 | Walker |
| 4,261,244 A | 4/1981 | Becht et al. |
| 4,317,451 A | 3/1982 | Cerwin et al. |
| 4,399,810 A | 8/1983 | Samuels et al. |
| 4,407,286 A | 10/1983 | Noiles et al. |
| 4,410,125 A | 10/1983 | Noiles et al. |
| 4,428,376 A | 1/1984 | Mericle |
| 4,430,998 A | 2/1984 | Harvey et al. |
| 4,434,796 A | 3/1984 | Karapetian et al. |
| 4,454,875 A | 6/1984 | Pratt et al. |
| 4,467,805 A | 8/1984 | Fukuda |
| 4,485,816 A | 12/1984 | Krumme |
| 4,485,953 A | 12/1984 | Rothfuss |
| 4,493,322 A | 1/1985 | Becht |
| 4,505,273 A | 3/1985 | Braun et al. |
| 4,506,669 A | 3/1985 | Blake, III |
| 4,508,253 A | 4/1985 | Green |
| 4,513,746 A | 4/1985 | Aranyi et al. |
| 4,526,173 A | 7/1985 | Sheehan |
| 4,526,174 A | 7/1985 | Froehlich |
| 4,534,352 A | 8/1985 | Korthoff |
| 4,535,772 A | 8/1985 | Sheehan |
| 4,548,202 A | 10/1985 | Duncan |
| 4,557,265 A | 12/1985 | Andersson |
| 4,566,620 A | 1/1986 | Green et al. |
| 4,568,009 A | 2/1986 | Green |
| 4,570,623 A | 2/1986 | Ellison et al. |
| 4,573,622 A | 3/1986 | Green et al. |
| 4,583,670 A | 4/1986 | Alvarado |
| 4,592,498 A | 6/1986 | Braun et al. |
| 4,593,843 A | 6/1986 | Saravis |
| 4,596,350 A | 6/1986 | Smith et al. |
| 4,607,638 A | 8/1986 | Crainich |
| 4,610,251 A | 9/1986 | Kumar |
| 4,618,086 A | 10/1986 | Li et al. |
| 4,619,262 A | 10/1986 | Taylor |
| 4,637,380 A | 1/1987 | Orejola |
| 4,646,741 A | 3/1987 | Smith |
| 4,655,222 A | 4/1987 | Florez et al. |
| 4,665,916 A | 5/1987 | Green |
| 4,671,279 A | 6/1987 | Hill |
| 4,676,245 A | 6/1987 | Fukuda |
| 4,696,300 A | 9/1987 | Anderson |
| 4,719,917 A | 1/1988 | Barrows et al. |
| 4,728,020 A | 3/1988 | Green et al. |
| 4,741,337 A | 5/1988 | Smith et al. |
| 4,752,024 A | 6/1988 | Green et al. |
| 4,753,636 A | 6/1988 | Free |
| 4,762,260 A | 8/1988 | Richards et al. |
| 4,776,506 A | 10/1988 | Green |
| 4,789,090 A | 12/1988 | Blake, III |
| 4,802,478 A | 2/1989 | Powell |
| 4,887,601 A | 12/1989 | Richards |
| 4,887,756 A * | 12/1989 | Puchy .............................. 227/19 |
| 4,895,148 A | 1/1990 | Bays et al. |
| 4,899,745 A | 2/1990 | Laboureau et al. |
| 4,915,100 A | 4/1990 | Green |
| 4,924,866 A | 5/1990 | Yoon |
| 4,955,898 A | 9/1990 | Matsutani et al. |
| 4,969,591 A | 11/1990 | Richards et al. |
| 4,976,686 A | 12/1990 | Ball et al. |
| 4,976,715 A | 12/1990 | Bays et al. |
| 4,994,073 A | 2/1991 | Green |
| 5,002,562 A | 3/1991 | Oberlander |
| 5,007,921 A | 4/1991 | Brown |
| 5,015,252 A | 5/1991 | Jones |
| 5,026,390 A | 6/1991 | Brown |
| 5,035,692 A | 7/1991 | Lyon et al. |
| 5,044,540 A | 9/1991 | Dulebohn |
| 5,047,047 A | 9/1991 | Yoon |
| 5,058,315 A | 10/1991 | Wagner |
| 5,062,563 A | 11/1991 | Green et al. |
| 5,078,731 A | 1/1992 | Hayhurst |
| 5,080,665 A | 1/1992 | Jarrett et al. |
| 5,089,009 A | 2/1992 | Green |
| 5,108,422 A | 4/1992 | Green et al. |
| 5,129,570 A | 7/1992 | Schulze et al. |
| 5,156,609 A | 10/1992 | Nakao et al. |
| 5,158,566 A | 10/1992 | Pianetti |
| 5,158,567 A | 10/1992 | Green |
| 5,160,339 A | 11/1992 | Chen et al. |
| 5,179,964 A | 1/1993 | Cook |
| 5,211,644 A | 5/1993 | VanBeek et al. |
| 5,211,722 A | 5/1993 | Wagner |
| 5,236,440 A | 8/1993 | Hlavacek |
| 5,257,713 A | 11/1993 | Green et al. |
| 5,258,009 A | 11/1993 | Conners |
| 5,258,010 A | 11/1993 | Green et al. |
| 5,258,012 A | 11/1993 | Luscombe et al. |
| 5,263,973 A | 11/1993 | Cook |
| 5,269,783 A | 12/1993 | Sander |
| 5,269,792 A | 12/1993 | Kovac et al. |
| 5,285,944 A | 2/1994 | Green et al. |
| 5,292,326 A | 3/1994 | Green et al. |
| 5,293,881 A | 3/1994 | Green et al. |
| 5,297,714 A | 3/1994 | Kramer |
| 5,304,204 A | 4/1994 | Bregen |
| 5,324,307 A | 6/1994 | Jarrett et al. |
| 5,337,937 A | 8/1994 | Remiszewski et al. |
| 5,342,376 A | 8/1994 | Ruff |
| 5,350,400 A | 9/1994 | Esposito et al. |
| 5,364,003 A | 11/1994 | Williamson, IV |
| 5,366,134 A | 11/1994 | Green et al. |
| 5,389,102 A | 2/1995 | Green et al. |
| 5,392,979 A | 2/1995 | Green et al. |
| 5,398,861 A | 3/1995 | Green |
| D357,316 S | 4/1995 | Green et al. |
| 5,413,584 A | 5/1995 | Schulze |
| 5,415,334 A | 5/1995 | Williamson, IV et al. |
| 5,417,361 A | 5/1995 | Williamson, IV |
| 5,423,856 A | 6/1995 | Green |
| 5,456,401 A | 10/1995 | Green et al. |
| 5,478,003 A | 12/1995 | Green et al. |
| 5,480,089 A | 1/1996 | Blewett |
| 5,482,197 A | 1/1996 | Green et al. |
| 5,489,058 A | 2/1996 | Plyley et al. |
| 5,489,287 A | 2/1996 | Green et al. |
| 5,505,363 A | 4/1996 | Green et al. |
| 5,509,596 A | 4/1996 | Green et al. |
| 5,514,149 A | 5/1996 | Green et al. |
| 5,542,594 A | 8/1996 | McKean et al. |
| 5,544,802 A | 8/1996 | Crainich |
| 5,549,619 A | 8/1996 | Peters et al. |
| 5,551,622 A | 9/1996 | Yoon |
| 5,558,266 A | 9/1996 | Green et al. |
| 5,562,241 A | 10/1996 | Knodel et al. |
| 5,571,285 A | 11/1996 | Chow et al. |
| 5,573,541 A | 11/1996 | Green et al. |
| 5,579,978 A | 12/1996 | Green et al. |
| 5,584,859 A | 12/1996 | Brotz |
| 5,591,178 A | 1/1997 | Green et al. |
| 5,593,423 A | 1/1997 | Person et al. |
| 5,618,311 A | 4/1997 | Gryskiewicz |
| 5,645,567 A | 7/1997 | Crainich |
| 5,658,312 A | 8/1997 | Green et al. |
| 5,662,258 A | 9/1997 | Knodel et al. |
| 5,662,655 A | 9/1997 | Laboureau et al. |
| 5,667,527 A | 9/1997 | Cook |

| | | |
|---|---|---|
| 5,706,997 A | 1/1998 | Green et al. |
| 5,725,538 A | 3/1998 | Green et al. |
| 5,725,554 A | 3/1998 | Simon et al. |
| 5,728,108 A | 3/1998 | Griffiths et al. |
| 5,794,834 A | 8/1998 | Hamblin et al. |
| 5,816,471 A | 10/1998 | Plyley et al. |
| 5,829,662 A | 11/1998 | Allen et al. |
| 5,871,135 A | 2/1999 | Williamson, IV et al. |
| 5,878,937 A | 3/1999 | Green et al. |
| 5,902,319 A | 5/1999 | Daley |
| 5,908,427 A | 6/1999 | McKean et al. |
| 5,947,999 A | 9/1999 | Groiso |
| 5,964,774 A | 10/1999 | McKean et al. |
| 5,976,160 A | 11/1999 | Crainich |
| 5,984,949 A | 11/1999 | Levin |
| 5,993,476 A | 11/1999 | Groiso |
| 6,045,560 A | 4/2000 | McKean et al. |
| 6,083,242 A | 7/2000 | Cook |
| 6,090,131 A | 7/2000 | Daley |
| 6,120,526 A | 9/2000 | Daley |
| 6,131,789 A | 10/2000 | Schulze et al. |
| 6,149,658 A | 11/2000 | Gardiner et al. |
| 6,159,224 A | 12/2000 | Yoon |
| 6,241,747 B1 | 6/2001 | Ruff |
| 6,250,532 B1 | 6/2001 | Green et al. |
| 6,270,517 B1 | 8/2001 | Brotz |
| 6,325,805 B1 | 12/2001 | Ogilvie et al. |
| 6,387,104 B1 | 5/2002 | Pugsley et al. |
| 6,387,113 B1 | 5/2002 | Hawkins et al. |
| 6,409,743 B1 | 6/2002 | Fenton, Jr. |
| 6,423,088 B1 | 7/2002 | Fenton, Jr. |
| 6,599,310 B2 | 7/2003 | Leung et al. |
| 6,619,529 B2 | 9/2003 | Green et al. |
| 6,626,916 B1 | 9/2003 | Yeung et al. |
| 6,629,988 B2 | 10/2003 | Weadock |
| 6,638,297 B1 | 10/2003 | Huitema |
| 6,692,499 B2 * | 2/2004 | Tormala et al. .............. 606/213 |
| 6,726,705 B2 | 4/2004 | Peterson |
| 6,773,437 B2 | 8/2004 | Ogilvie et al. |
| 7,112,214 B2 | 9/2006 | Peterson |
| D532,107 S | 11/2006 | Peterson |
| 2002/0007184 A1 | 1/2002 | Ogilvie et al. |
| 2002/0019636 A1 | 2/2002 | Ogilvie et al. |
| 2002/0133181 A1 | 9/2002 | Tong |
| 2003/0236551 A1 | 12/2003 | Peterson |
| 2004/0059377 A1 | 3/2004 | Peterson |
| 2005/0033317 A1 | 2/2005 | Ables |
| 2005/0085857 A1 | 4/2005 | Peterson |
| 2005/0182444 A1 | 8/2005 | Peterson |

FOREIGN PATENT DOCUMENTS

| | | |
|---|---|---|
| JP | 04-226642 A | 8/1992 |
| JP | 5-504892 | 7/1993 |
| JP | 7-124166 | 5/1995 |
| JP | 2000-217829 | 8/2000 |
| JP | 2000-517197 | 12/2000 |
| WO | WO 97/18761 | 5/1997 |
| WO | WO 00/57796 | 10/2000 |
| WO | WO 00/67644 | 11/2000 |

OTHER PUBLICATIONS

Brochure: *La Sutura Perde il Filo*, Farmitalia Carlo Erba, 4 pgs., not dated.

*Evaluation of New Absorbable Lactomer Subcuticular Staple*, G.C. Zachmann, P.A. Foresman, T.J. Bill, D.J. Bentrem, G.T. Rodeheaver, R.F. Edlich, Journal of Applied Biomaterial, vol. 5, No. 3, pp. 221-116, 1994.

Office Action dated Jul. 21, 2010 for U.S. Appl. No. 11/097,085, filed Apr. 1, 2005, 11 pages.

Notice of Allowance dated Sep. 27, 2010 for U.S. Appl. No. 10/607,497, filed Jun. 25, 2003.

EPO Communication dated Mar. 8, 2011 for EP Application No. 03761338.7 filed Jun. 25, 2003.

Office Action mailed Apr. 13, 2011 for U.S. Appl. No. 11/097,085, filed Apr. 1, 2005.

* cited by examiner

METHOD AND APPARATUS FOR TISSUE FASTENING WITH SINGLE TRANSLATING TRIGGER OPERATION

RELATED APPLICATIONS AND PRIORITY CLAIM

The present application is a continuation-in-part application of U.S. patent application Ser. No. 10/448,838, filed May 30, 2003, now U.S. Pat. No. 7,686,200, entitled "Mechanical Method and Apparatus for Bilateral Tissue Fastening," which is a divisional of U.S. patent application Ser. No. 10/179,628, filed Jun. 25, 2002, now issued as U.S. Pat. No. 6,726,705, and is also a continuation-in-part application of U.S. Continuation-In-Part application Ser. No. 10/607,497, entitled "Mechanical Method and Apparatus for Bilateral Tissue Fastening," filed Jun. 25, 2003, now U.S. Pat. No. 7,950,559, and U.S. Continuation-In-Part application Ser. No. 10/603,397, entitled "Dynamic Bioabsorbable Fastener for Use in Wound Closure," filed Jun. 25, 2003, now U.S. Pat. No. 7,112,214, all of which are herein incorporated by reference in their entirety.

FIELD OF THE INVENTION

The present invention relates generally to the field of surgical instruments such as surgical staplers, clip applicators and sutureless closure devices. More particularly, the present invention relates to a mechanical method and apparatus for fastening tissue, such as skin tissue, with a fastener that secures opposed pieces of tissue and is deployed by a single translating trigger operation.

BACKGROUND OF THE INVENTION

Biological healing of a tissue opening commences through the proximity of the opposed living tissue surfaces. If the opening is very large or if its location subjects the wound to continual movement, a physician will seek to forcibly hold the sides of the opening in close proximity so as to promote the healing process.

Human skin tissue is comprised of three distinct layers of tissue. The epidermal layer, also known as the epidermis, is the outermost layer and includes non-living tissue cells. The dermal layer, or dermis, is the middle layer directly below the epidermal layer and comprises the living tissue of the skin that is the strongest of the three layers. The subcutaneous, or hypodermis layer is the bottom layer of skin tissue and includes less connective tissue making this the weakest layer of skin tissue. Healing occurs best when the opposing dermal layers of the skin tissue are held in proximity with each other.

While traditional suturing remains a popular method of effectuating closure of wound openings, the use of staples and staplers as a closure technique has become increasingly popular, especially in surgical settings where the opening is created through a purposeful incision. In these settings, the incision tends to make a clean, straight cut with the opposing sides of the incision having consistent and non-jagged surfaces.

Prior art methods of closing tissue using a stapler require at least two hands. For example, when stapling a skin opening, a medical professional typically uses one hand to manually approximate the opposing sides of the skin opening while another hand is used to position the stapler so that a metal staple will span the opening. The stapler is then manipulated such that the staple is driven into the skin with one leg being driven into each side of the skin and the cross-member of the staple extending across the opening external to the skin surface. Generally, the legs of a metal staple are driven into an anvil causing the metal staple to deform so as to retain the skin tissue in a compressed manner within the staple. This process can be repeated along the length of the wound opening such that the entire incision or wound is held closed during the healing process.

While effective in holding an incision or wound closed, conventional metal staples unfortunately require removal after the healing process of a wound opening is completed. As the sciences of medical and materials technology have advanced over the course of the past century, new bioabsorbable polymers and copolymers have been developed that provide medical professionals with an alternative to metal staples that must be removed. Fasteners made of bioabsorbable materials, sometimes referred to as bioabsorbable or biodegradable, break down or degrade over time in the body, with the residuals being either absorbed or ultimately expelled by the body's natural processes.

Bioabsorbable polymer fasteners are preferable to metal staples because they do not have to be removed. While there has been active development of dermal layer suturing techniques, little has been done in the area of staples and staplers for use in connection with the dermal layer. In a series of patents issued to Green et al., including U.S. Pat. Nos. 5,292,326, 5,389,102, 5,489,287 and 5,573,541, a subcuticular stapling method and apparatus are disclosed that were ultimately commercialized as the U.S. Surgical SQS Subcuticular Stapling Apparatus. The Green et al., patents describe a stapling technique employing a handheld apparatus with jaws to proximate, interdigitate and overlap opposing sides of dermal layer tissue along the length of a skin opening. The apparatus then drives a single spike through the interdigitated and overlapped dermal layers of the opposing skin surfaces in order to secure both sides of the dermal tissue on the single spike. The trigger assembly for this apparatus utilizes a conventional reciprocating trigger arrangement whereby the direction of squeezing action of the trigger is generally parallel to and opposite of the direction in which the spike is ejected from the fastener. Although this technique reduced the time required to effectuate a subcuticular skin closure, the SQS device was not commercially successful in part because the resulting closure produced an undesirable wave-like scar that sometimes did not heal effectively.

A novel bilateral approach to fastening dermal tissue using bioabsorbable fasteners is disclosed and described in U.S. Pat. No. 6,726,705, as well as in U.S. patent application Ser. Nos. 10/448,838, 10/607,497 and 10/603,397, to Peterson et al, all of which are commonly assigned to the assignee of the present application and all of which are incorporated by reference in their entirety. In one embodiment, this bilateral approach to tissue fastening utilizes a first apparatus to manipulate opposed sides of tissue to form target tissue zones followed by a second apparatus that effects a bilateral insertion of a tissue fastener to retain opposed dermal layers across an incision or wound in close approximation to facilitate healing. By maintaining contact of the dermal layers through the healing process, the healing process is enhanced which results in less chance of infection, faster recovery and improved aesthetic appearance. In addition, no subsequent medical follow-up is necessary to remove fasteners as is typically necessary with nonabsorbable fasteners. In this embodiment of Peterson et al., however, two medical practitioners may be required, one for operating each of the two apparatus that are utilized to accomplish bilateral capture and insertion of the bioabsorbable fastener.

While the bilateral tissue fastening methods and apparatus taught by Peterson et al. provide many advantages, there are opportunities to improve upon the principles taught by Peterson et al. with respect to tissue fastening applications. For example, it would be desirable to provide for a fastening device that can be operated more effectively by a single medical practitioner with one hand to repeatedly and accurately approximate tissue while deploying staples.

SUMMARY OF THE INVENTION

The invention includes a mechanical device and method for gathering and securing tissue with a fastener. The device includes an applicator assembly operably configured to deploy a fastener in a first direction, a tissue manipulation assembly operably configured to move from a relaxed position to a grasping position in a second direction generally transverse to the first direction, and a translating trigger assembly operably coupled to the applicator assembly and the tissue manipulation assembly. The trigger assembly is operably configured to move from a relaxed position, through a first position, to a second position along a third direction that is generally transverse to both the first direction and the second direction, such that manual operation of the translating trigger assembly from the relaxed position through the first position along the third direction causes the tissue manipulation assembly to move in the second direction to gather at least portion of the opposed tissue. Continued manual operation of the translating trigger assembly from the first position on to the second position along the third direction causes the applicator assembly to deploy the fastener into the opposed tissue along the first direction.

In another embodiment, the invention includes a method for gathering and securing opposed tissue with a fastener. The method includes providing a fastener apparatus having an applicator assembly operably configured to deploy a fastener in a first direction, a tissue manipulation assembly operably configured to move from a relaxed position to a grasping position in a second direction generally transverse to the first direction, and a translating trigger assembly operably coupled to the applicator assembly and the tissue manipulation assembly. The trigger assembly is operably configured to move from a relaxed position, through a first position, to a second position along a third direction that is generally transverse to both the first direction and the second direction. The method also includes the steps of positioning at least a portion of the applicator assembly in an interface between the opposed tissue, advancing the trigger assembly from the relaxed position through the first position along the third direction wherein the tissue manipulation assembly moves in the second direction to gather a portion of the tissue, and moving the trigger assembly from the first position to the second position along the third direction wherein the applicator assembly deploys the fastener into opposed tissue along the first direction.

In yet another embodiment, the invention includes a device for gathering and securing opposed tissue with a fastener. The device includes an applicator means operably configured to deploy a fastener in a first direction, a tissue manipulation means operably configured to move from a relaxed position to a grasping position in a second direction generally transverse to the first direction, and a translating trigger means operably coupled to the applicator means and the tissue manipulation means. The trigger means is operably configured to move from a relaxed position, through a first position, to a second position along a third direction that is generally transverse to both the first direction and the second direction such that manual operation of the translating trigger means from the relaxed position through the first position along the third direction causes the tissue manipulation means to move in the second direction to gather at least a portion of the opposed tissue, and such that continued manual operation of the translating trigger means from the first position on to the second position along the third direction causes the applicator means to deploy the fastener into the opposed tissue along the first direction.

In yet another embodiment, the invention includes a method for forming an interrupted closure of opposed tissue on adjacent sides of a wound. The method includes the steps of providing an apparatus having a plurality of fasteners, wherein the length of each of the plurality of fasteners is shorter than the longitudinal length of the wound, positioning at least a portion of the fastener apparatus in an interface between the opposed tissue, deploying a first fastener into subcutaneous tissue in a first direction without penetrating the epidermis of the tissue wherein, a single barb of the first fastener is located on each of the opposite sides of the wound, and inserting a second fastener into subcutaneous tissue in a first direction without penetrating the epidermis of the tissue wherein, a single barb of the second fastener is located on each of the opposite sides of the wound.

DETAILED DESCRIPTION OF THE PREFERRED EMBODIMENTS

FIGS. 1-4 show wound closure instrument 100. Instrument 100 can take the form of the Insorb® Subcuticular Stapler as supplied by Incisive Surgical, Inc. of Plymouth, Minn., and as further described in U.S. Pat. No. 6,726,705 and pending U.S. patent application Ser. Nos. 10/448,838, 10/607,497 and 29/202,831, all of which are incorporated by reference in their entirety.

Figure 1:
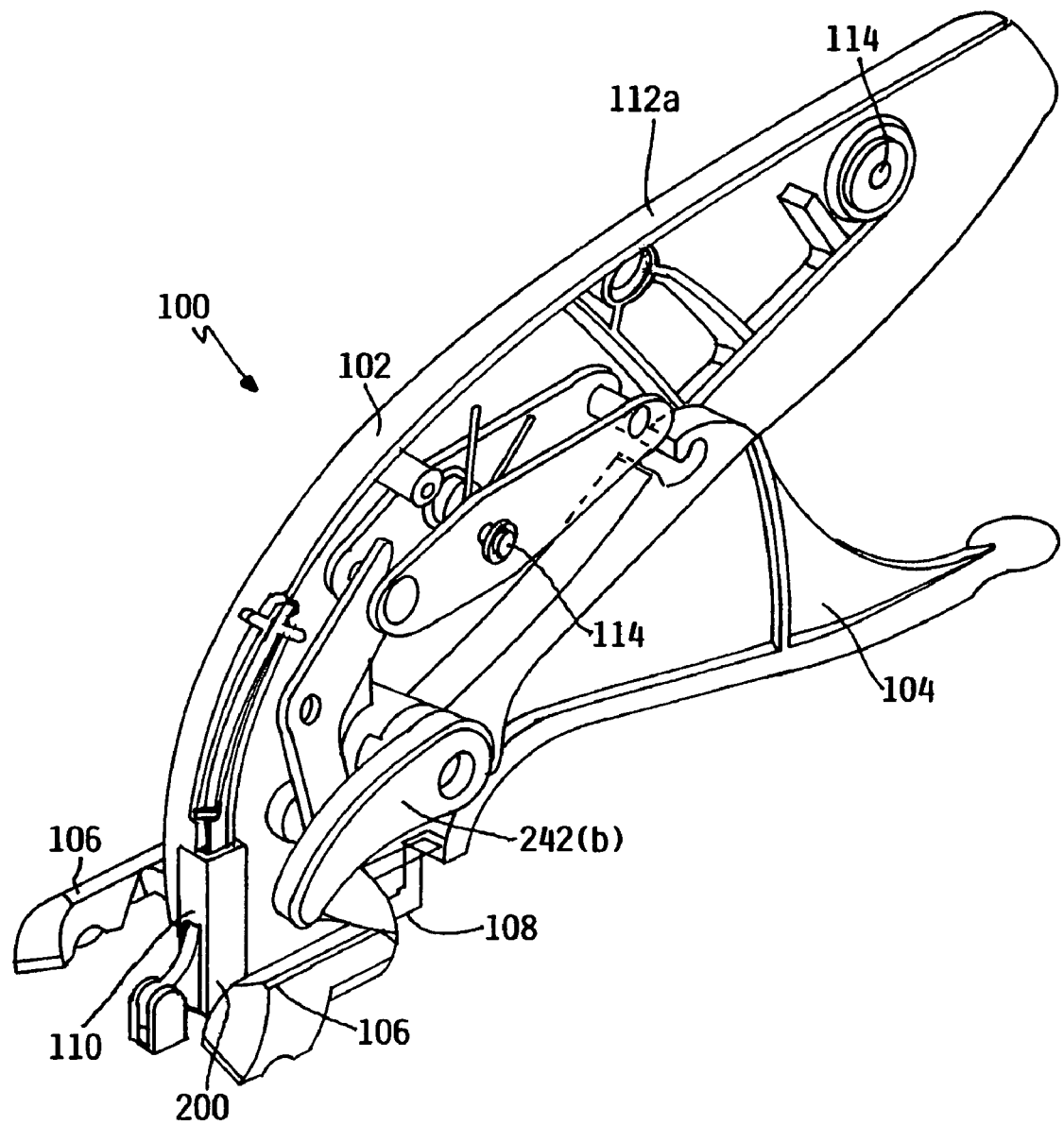
FIG. 1 shows a perspective view of a wound closure instrument incorporating the present invention.
Figure 2:
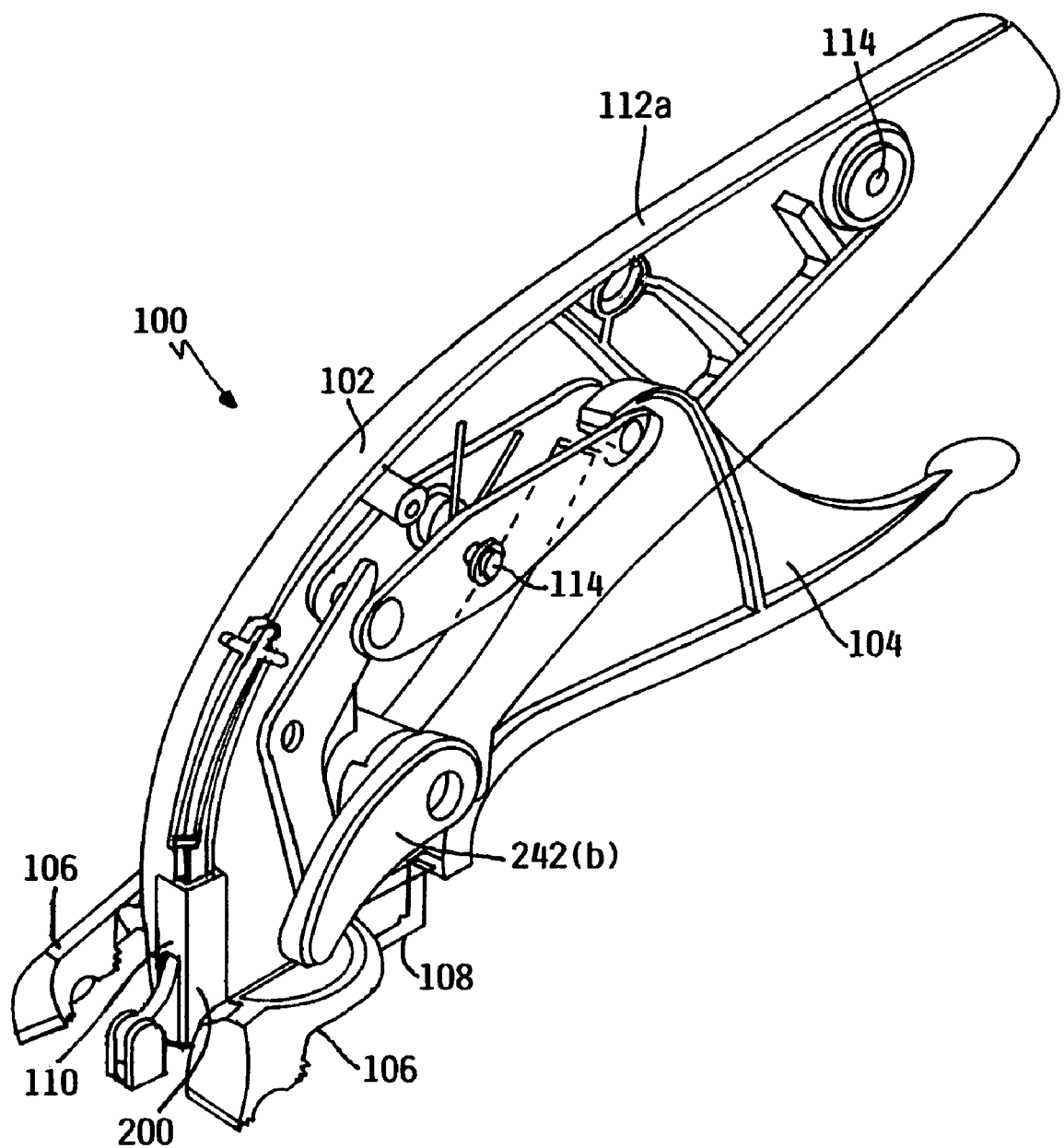
FIG. 2 is a perspective view of a wound closure instrument showing the trigger in a first position.
Figure 3:
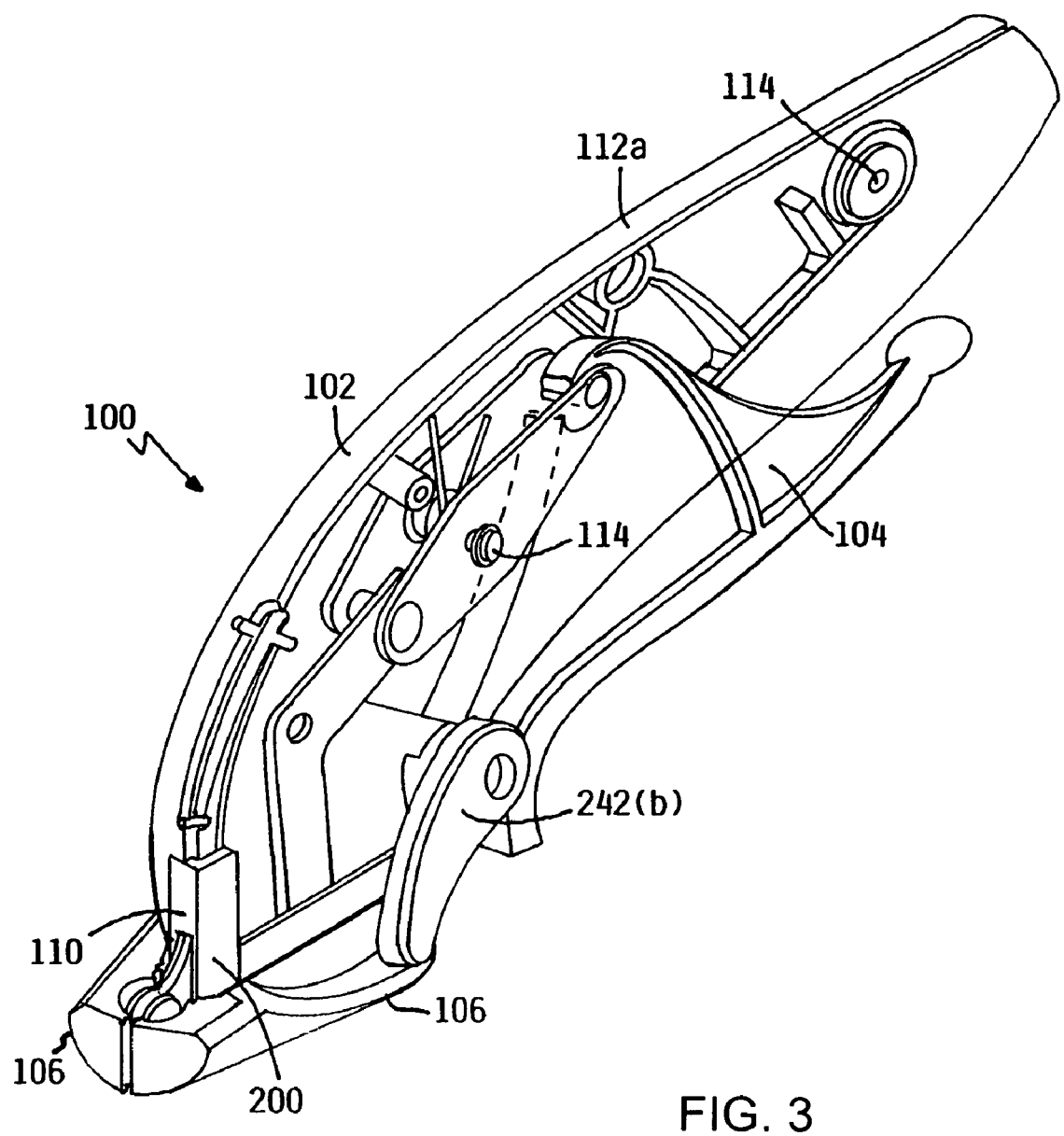
FIG. 3 is a perspective view of a wound closure instrument showing the trigger in a second position.
Figure 4:
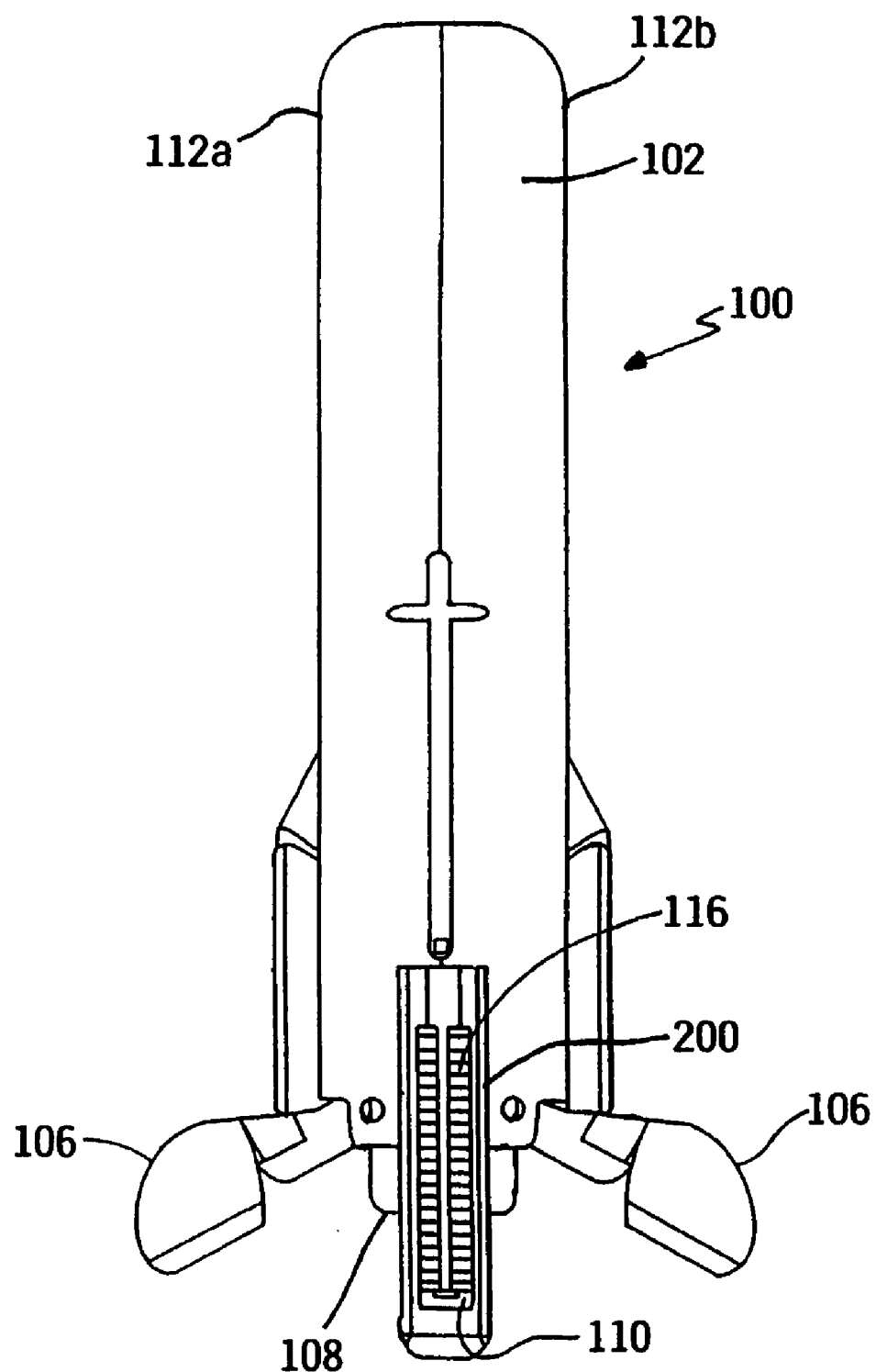
FIG. 4 shows a front view of a wound closure instrument incorporating the present invention.
Figure 4A:
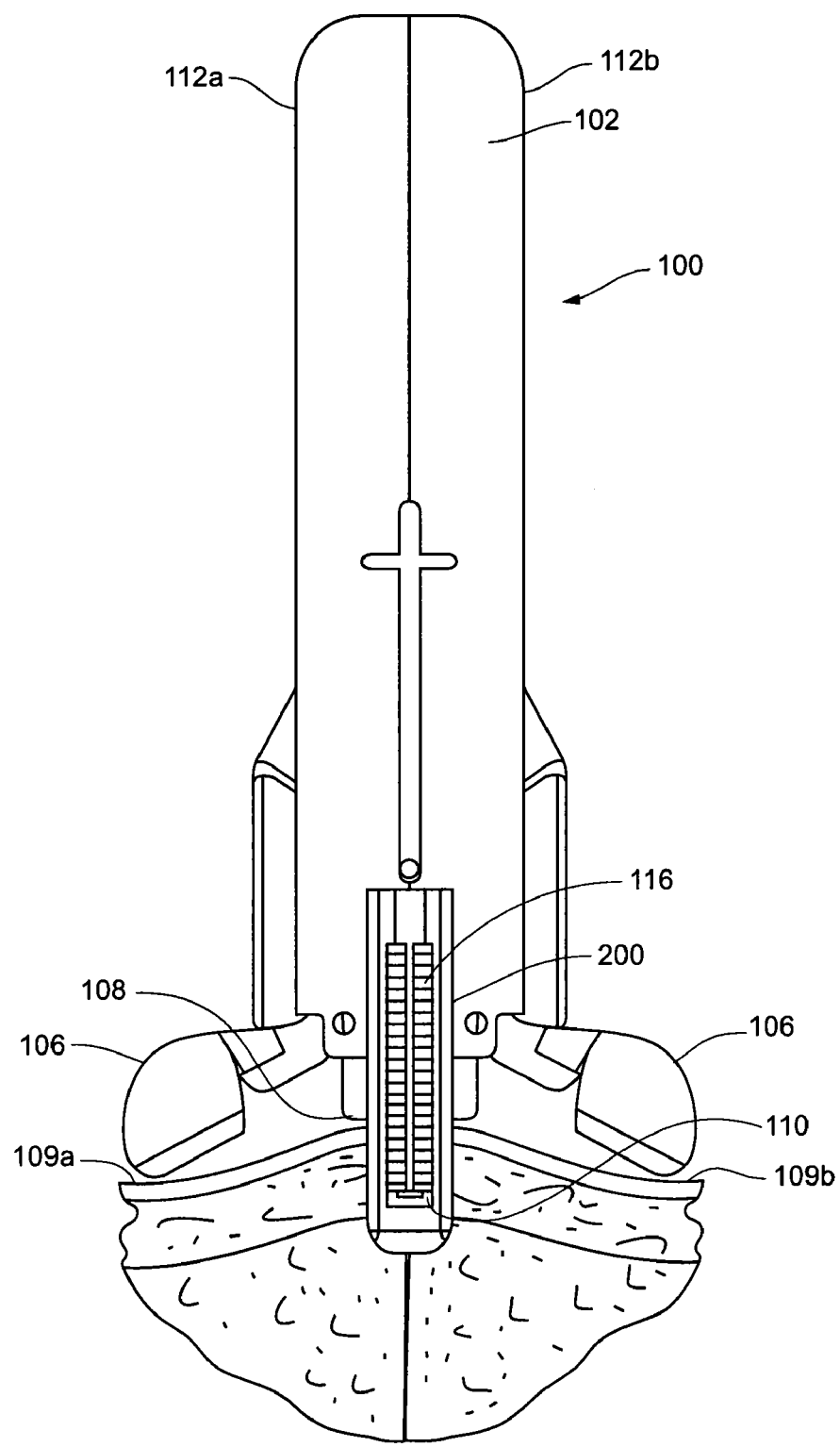
FIG. 4a shows a front view a wound closure instrument including a head portion positioned within in an interface between opposed tissue according to the present invention.
Figure 5:
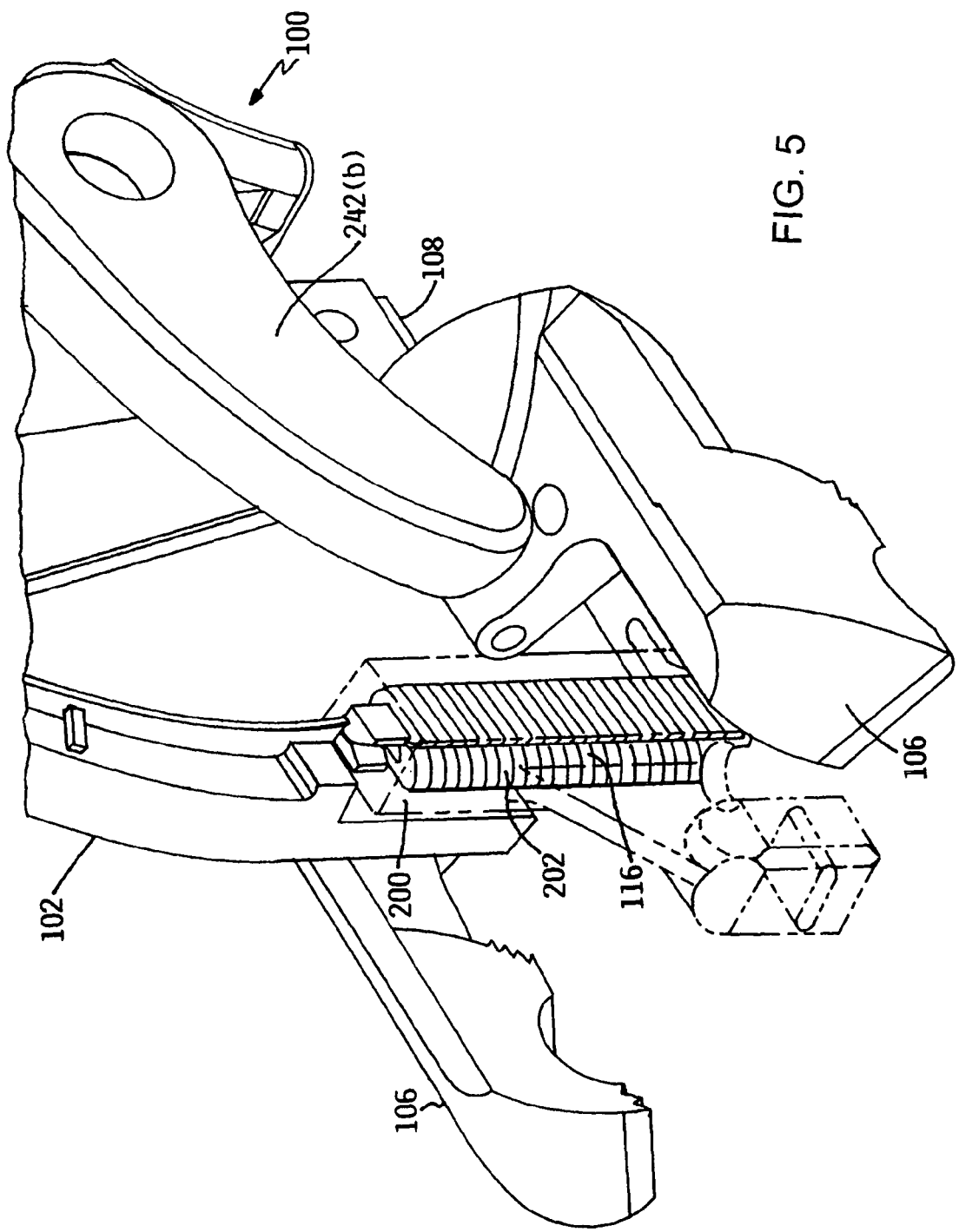
FIG. 5 shows an enlarged perspective view of a wound closure instrument incorporating the present invention.
Figure 6:
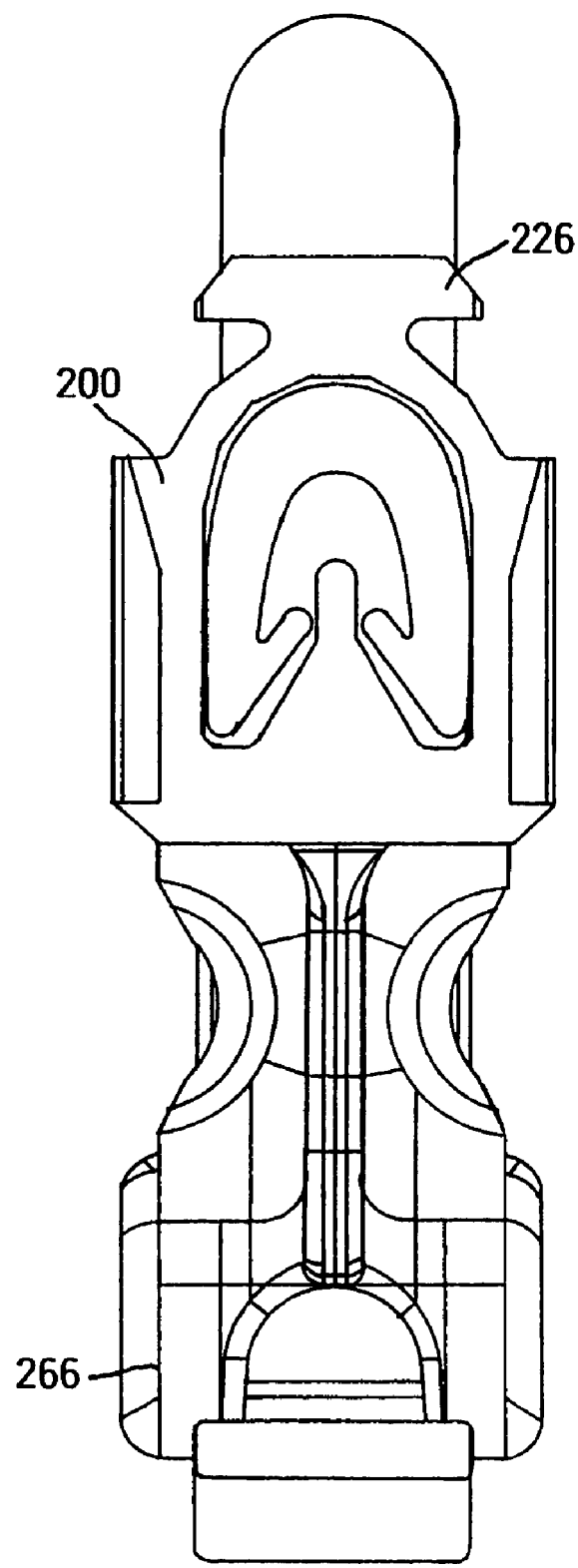
FIG. 6 shows a top view of the cartridge of the present invention.

Wound closure instrument 100 is comprised of body assembly 102, a trigger assembly 104, a tissue manipulation assembly 106, an applicator assembly 108, and a fastener assembly 110. Trigger assembly 104 is capable of moving from a relaxed position as shown in FIG. 1, to a first position as shown in FIG. 2, to a second position as shown in FIG. 3. Trigger assembly 104 incorporates a two-stage mechanism sequentially operating both the tissue manipulation assembly 106 and applicator assembly 108 as shown in FIGS. 1-3 and FIG. 16. At least a portion of applicator assembly 108 is adapted to be positioned in an interface between two sides of opposed tissue 109a, 109b as shown in FIG. 4a.

Figure 18:
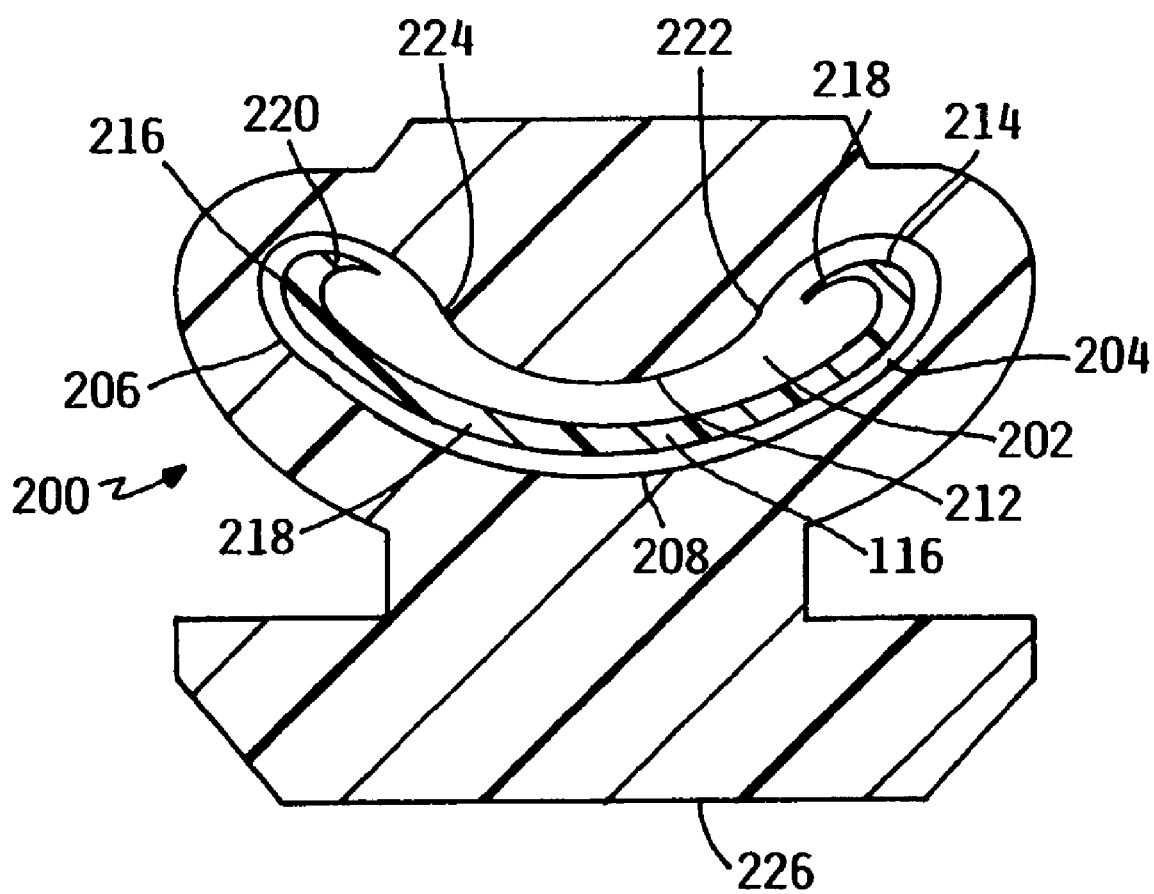
FIG. 18 is a partial cross-sectional view of an alternative embodiment of the cartridge of the present invention.

To grasp tissue with tissue manipulation assembly 106, an operator grasps instrument 100 so that the operator's fingers are disposed around trigger 104 and palm is against body assembly 102. Next, the operator positions tissue manipulation assembly so that skin tissue is vertically aligned between tissue gatherers 246(a) and 246(b). The operator then squeezes trigger assembly 104 toward body assembly 102. This action causes trigger 238 to rotate about ratchet member 240. As trigger 238 enters body assembly 102, connecting arms 242a, 242b rotate to contact the guide ramp 244 on tissue gatherers 246a and 246b causing tissue gatherers 246a, 246b to rotate to the position shown in FIG. 2. In this position, skin tissue becomes disposed between tissue gatherers 246a and 246b. As tissue gatherers 246(a), 246(b) rotate to a grasping position on either side of cartridge 200 as shown in FIG. 18, the skin tissue is held firmly in place.

The tissue gatherers 246a and 246b of the preferred embodiment capture the skin tissue and prepare it for staple insertion. When used in connection with thin or moist skin, it is especially important that the tissue gatherers 246a and 246b perform the dual function of minimizing movement of the skin tissue during staple insertion. Accordingly, it is desirable for the capture surface 282 to be rough so that the movement of skin tissue can be minimized during staple insertion. For example capture surface 282 can include a plurality of small dimples. Alternatively, capture surface 282 can include a plurality of small bumps or protrusions. In another embodiment, capture surface 282 can include a plurality of jagged grooves. In yet another embodiment, an adhesive may be disposed on capture surface 282. In still another embodiment, capture surface 282 can include a suction device to create a vacuum between skin tissue and capture surface 282 while a staple is inserted.

Following manipulation of tissue gatherers 246(a), 246(b) to the grasping position shown in FIG. 3, further squeezing of body assembly 102 and trigger assembly 104 causes trigger 238 to move further into body assembly 102 such that interface channel 250 slides around distal connector 252. As trigger 238 inserts further into body assembly 102, distal connector 252 reaches the end of interface channel 250 causing rotatable member 254 to rotate about fulcrum 256 such that proximal connector 258 moves in a downward direction. Downward movement of proximal connector 258 causes channel 260 to move in a downward direction resulting in rotatable member 254 rotating about fulcrum 256. As channel 260 moves downward, connecting tip 262 moves in a forward direction causing insertion slide 264 to advance toward insertion head 266. As insertion head 266 advances, piercing members 268(a), 268(b) and backspan member 270 cooperatively capture a bottom most fastener from the plurality of fasteners 116. The bottom-most fastener is advanced through the capture zone 272 and into the target tissue zones 274.

Once trigger assembly 104 is released, the pressure from spring 276 moves trigger 238 out of body assembly 102. This enables ratchet member 240 to also release. Next, piercing members 268(a), 268(b) retract past the plurality of fasteners 116 and biasing member 230 and rod 228 advances the bottom most fastener into position for a future capture by piercing members 268(a), 268(b). As ratchet member 240 releases, spring 276 interacts with upper engagement portion 278 allowing trigger 238 to return to its original position which in turn causes tissue gatherers 246(a), 246(b) to release the grasped tissue. Accordingly, trigger assembly 104 and tissue manipulation assembly 106 return to the position shown in FIG. 1. Instrument 100 is then ready to repeat the grasping process and insert a subsequent staple.

Figure 16:
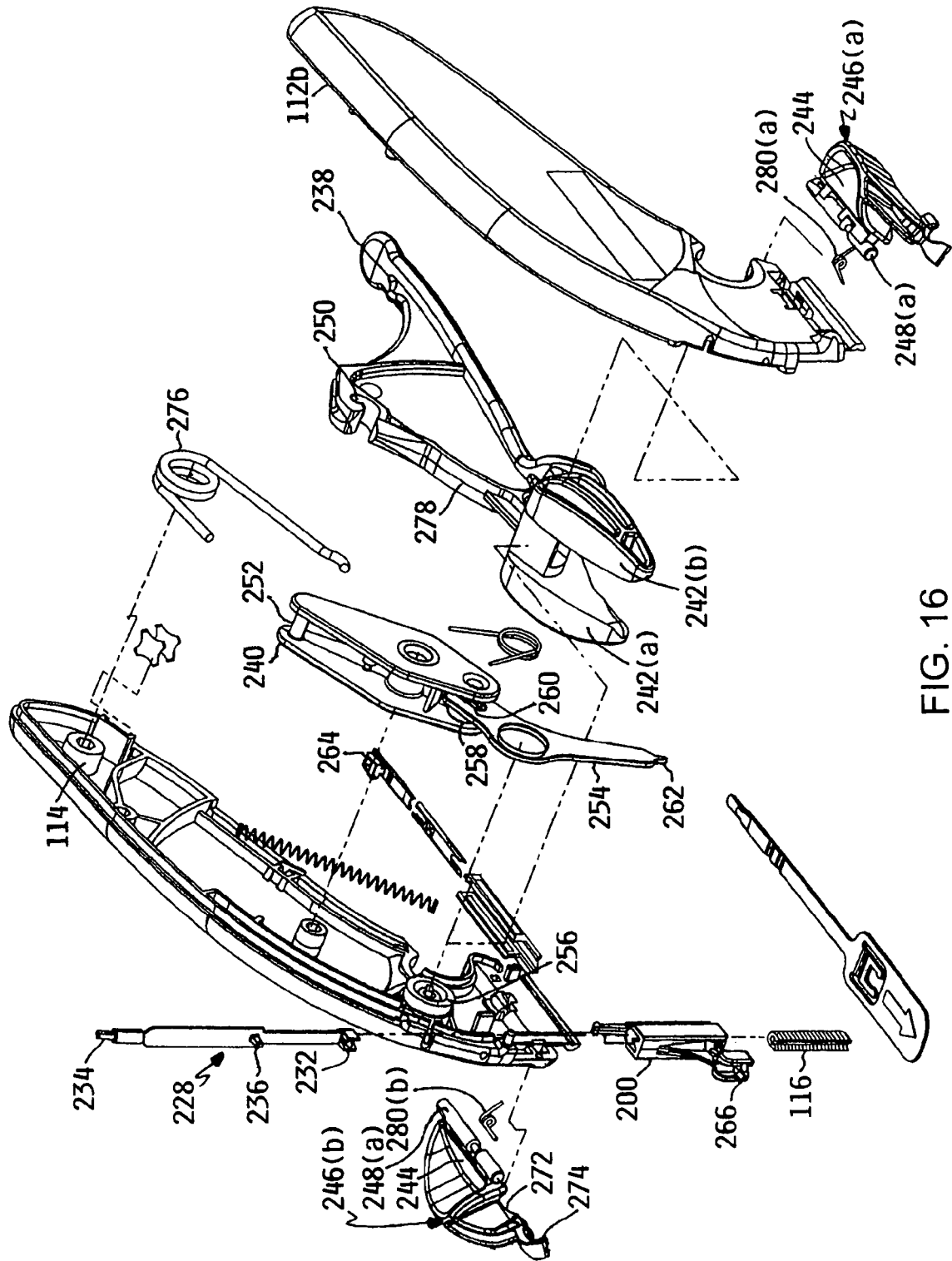
FIG. 16 is an exploded view of a wound closure instrument incorporating the present invention.
Figure 17:
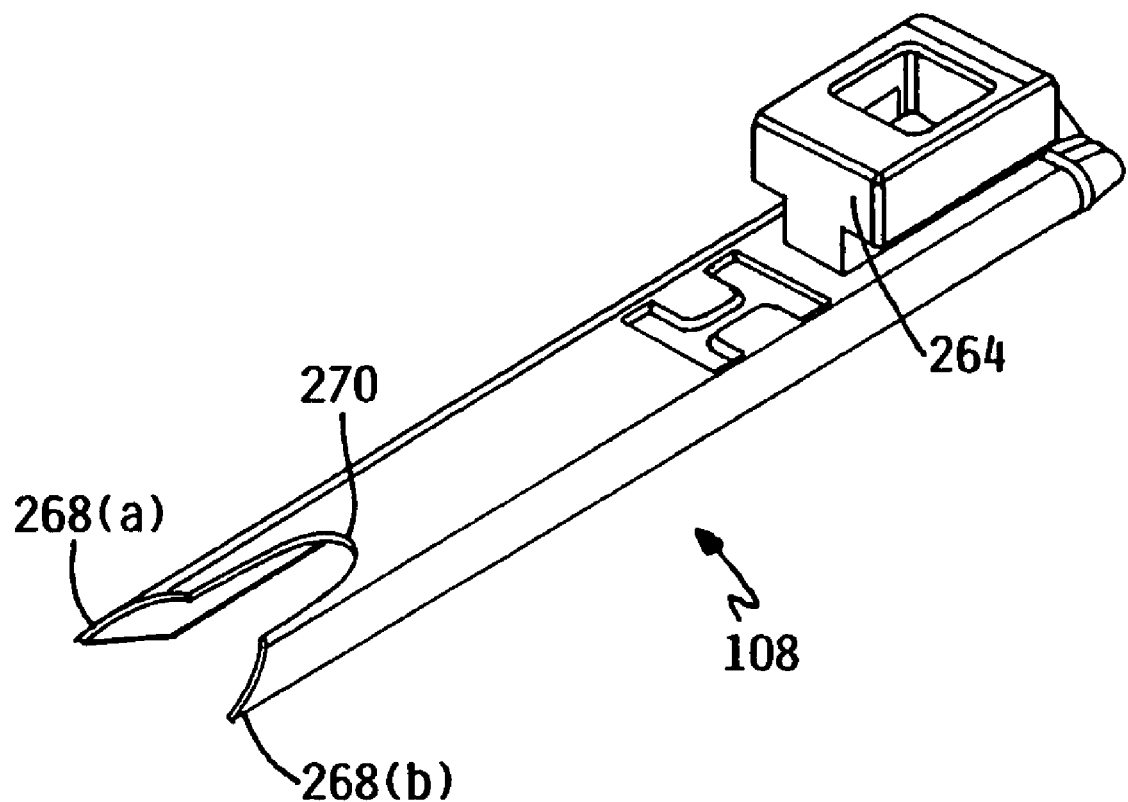
FIG. 17 is a perspective view of the applicator assembly in accordance with the present invention.

With reference to FIG. 16, the details of instrument 100 will now be discussed. Body assembly 102 preferably comprises a clam shell design with a first molded portion 112a and a second molded portion 112b that can be snapped together, thermally bonded, adhesively bonded or connected via a plurality of fastening members 114. Body assembly 102 is preferably fabricated from plastic, although a variety of materials may be used while remaining within the scope of the invention.

Fastener assembly 110 comprises a plurality of bioabsorbable fasteners 116, for example the dynamic bioabsorbable fasteners described in U.S. patent application Ser. No. 10/603,397, which is incorporated by reference in its entirety, and a fastener cartridge 200. Bioabsorbable fasteners 116 are stored within fastener cartridge 200 in a stacked configuration.

Figure 7:
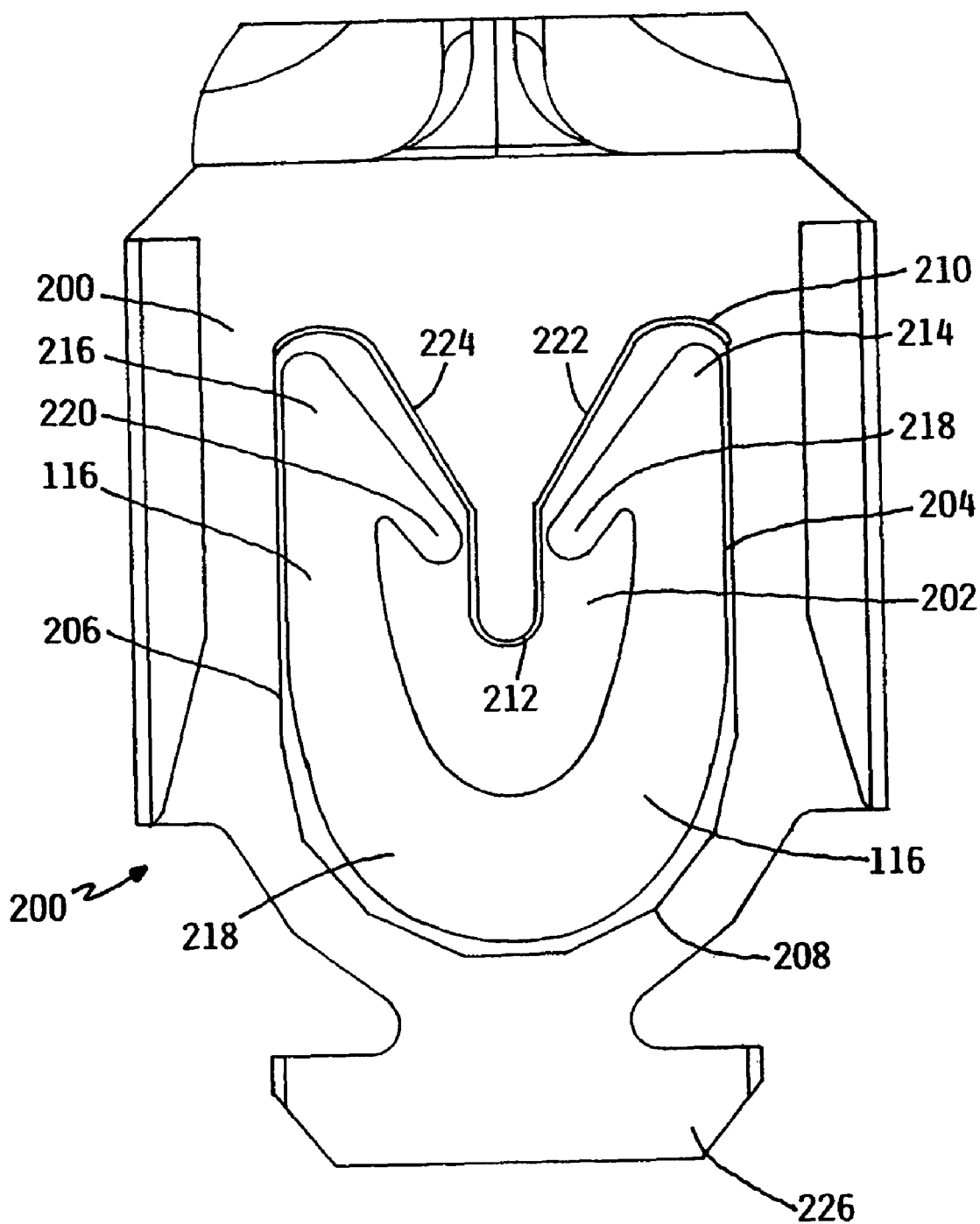
FIG. 7 shows a partial cross-sectional view of the cartridge of the present invention.
Figure 8:
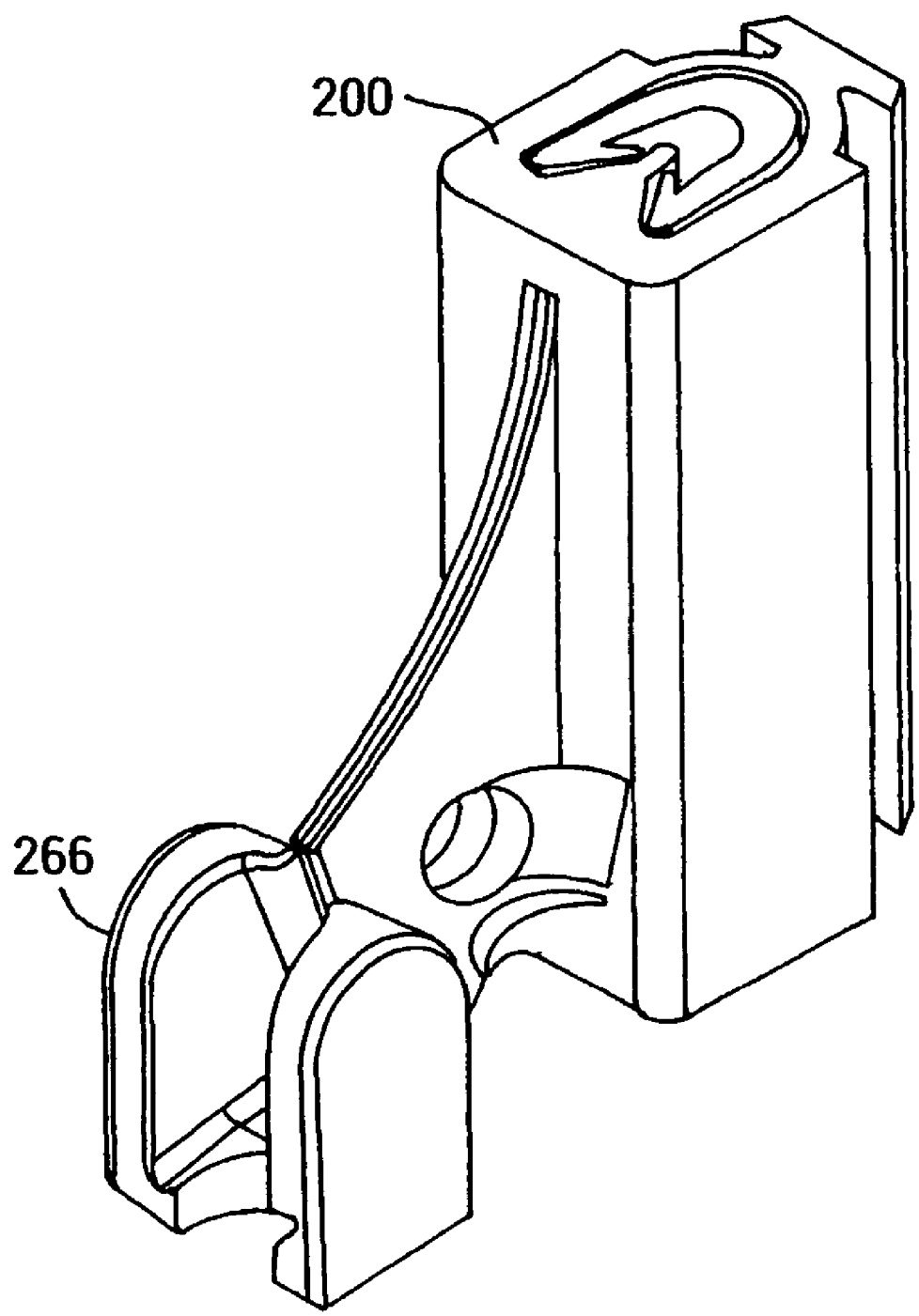
FIG. 8 shows a perspective view of the cartridge of the present invention.

Examples of bioabsorbable materials from which bioabsorbable fasteners 116 can be formed include poly(dl-lactide), poly(l-lactide), polyglycolide, poly(dioxanone), poly(glycolide-co-trimethylene carbonate), poly(l-lactide-co-glycolide), poly(dl-lactide-co-glycolide), poly(l-lactide-co-dl-lactide), poly(caprolactone) and poly(glycolide-co-trimethylene carbonate-co-dioxanone). Other polymer, synthetic or biological materials which are designed for initial structural integrity and have the capability of breaking down over time in the body could also be utilized. FIG. 7 shows a top cross-sectional view of the fasteners 116 disposed in the cartridge 200. Cartridge 200 includes a cavity 202 that is defined by a first surface 204, a second surface 206, a rear surface 208, and a forward surface 210. Forward surface 210 includes a protrusion 212 located at the midpoint of the forward surface 210. Protrusion 212 is shown extending into cavity 202, toward rear surface 208, between first surface 204 and second surface 206. In one embodiment, forward surface 210 includes kanted portions 222 and 224 extending toward protrusion 212.

The dimensions of a preferred embodiment of cavity 202 will now be discussed. Kanted portions 222 and 224 define an angle of between 30 and 90 degrees with respect to one another, preferably between 45 and 75 degrees, more preferably between 55 and 65 degrees. The width of protrusion 212 along the dimension extending into cavity 202 is between 0.010 and 0.042 inches, preferably between 0.018 and 0.034 inches. The width of cavity 202 from first surface 204 to second surface 206 is between 0.130 and 0.150 inches, preferably between 0.138 and 0.142 inches. The maximum height of cavity 202 from kanted portion 222 and rear surface 208 is between 0.190 and 0.210 inches, preferably between 0.197 and 0.203 inches. The distance between the tip of protrusion 212 and rear surface 208 is between 0.090 and 1.110 inches, preferably between 0.092 and 1.108 inches. The rear surface 208 defines a curve with a radius of between 0.060 and 0.080 inches, preferably between 0.065 and 0.075 inches, more preferably 0.070 inches.

FIG. 18 shows a top cross-sectional view of dynamic fasteners 216 disposed in an alternative embodiment of the cartridge 200. A description of dynamic fastener is disclosed in U.S. patent application Ser. No. 10/603,397, which is hereby incorporated by reference in its entirety. Cartridge 200 includes a cavity 202 that is defined by a first surface 204, a second surface 206, a rear surface 208, and a forward surface 210. Forward surface 210 includes a protrusion 212 located at the midpoint of the forward surface 210. Protrusion 212 is shown extending into cavity 202, toward rear surface 208, between first surface 204 and second surface 206. In one embodiment, forward surface 210 includes kanted portions 222 and 224 extending toward protrusion 212.

Fasteners 116 include a first tip 214, a second tip 216, and a body 218 that joins first tip 214 and second tip 216. In one embodiment, first tip 214 and second tip 216 include barbs 218 and 220, respectively.

In a preferred embodiment, fasteners 116 are constrained within cavity 202 by first surface 204 and second surface 206. This aspect of the invention is desirable for maintaining a constant distance between the first tip 214 and second tip 216. Fasteners 116 may also be constrained by any or all of the rear surface 208, forward surface 210, kanted portions 222, 224 and protrusion 212.

During operation and use, downward pressure is preferably applied to the plurality of fasteners 116 by rod 228 and biasing member 230. Rod 228 includes plug 232 configured to apply pressure to the plurality of fasteners 116 in cavity 202. Biasing member 230 couples with rod 228 at knob 234. The pressure generated by biasing member 230 against the interior of body assembly 102 and rod 228 generates a downward force by plug 232 against the plurality of fasteners 116. It will be recognized that other arrangements for application of a biasing force to the plurality of fasteners 116 could also be utilized whereby the function of the biasing member 230 and rod 228 are combined, such as a spring or a flexible metal member. Alternatively, other structures for applying a biasing force could be used in place of rod 228, such as a piston or a crossbar could be utilized.

Rod 228 includes a catch 236 that is configured to rest against a corresponding area of molded portion 112 or a removable lock 300. This enables instrument 100 to be shipped fully assembled to facilitate ease of use by a physician. Preferably, catch 236 and the removable lock 300 prevents biasing member 230 from applying force directly to fasteners 116 during shipment or storage so that the fasteners 116 do not deform after prolonged exposure to the spring force. Preferably, instrument 100 is a multi-shot design in which the plurality of fasteners 116 come preloaded in the cartridge 200 with the cartridge 200 assembled as part of the fastener assembly 110, thus eliminating any hand loading of individual fasteners. Alternatively, cartridge 200 may be preloaded or hand loaded and designed for insertion into fastener assembly 110 prior to use.

Figure 9:
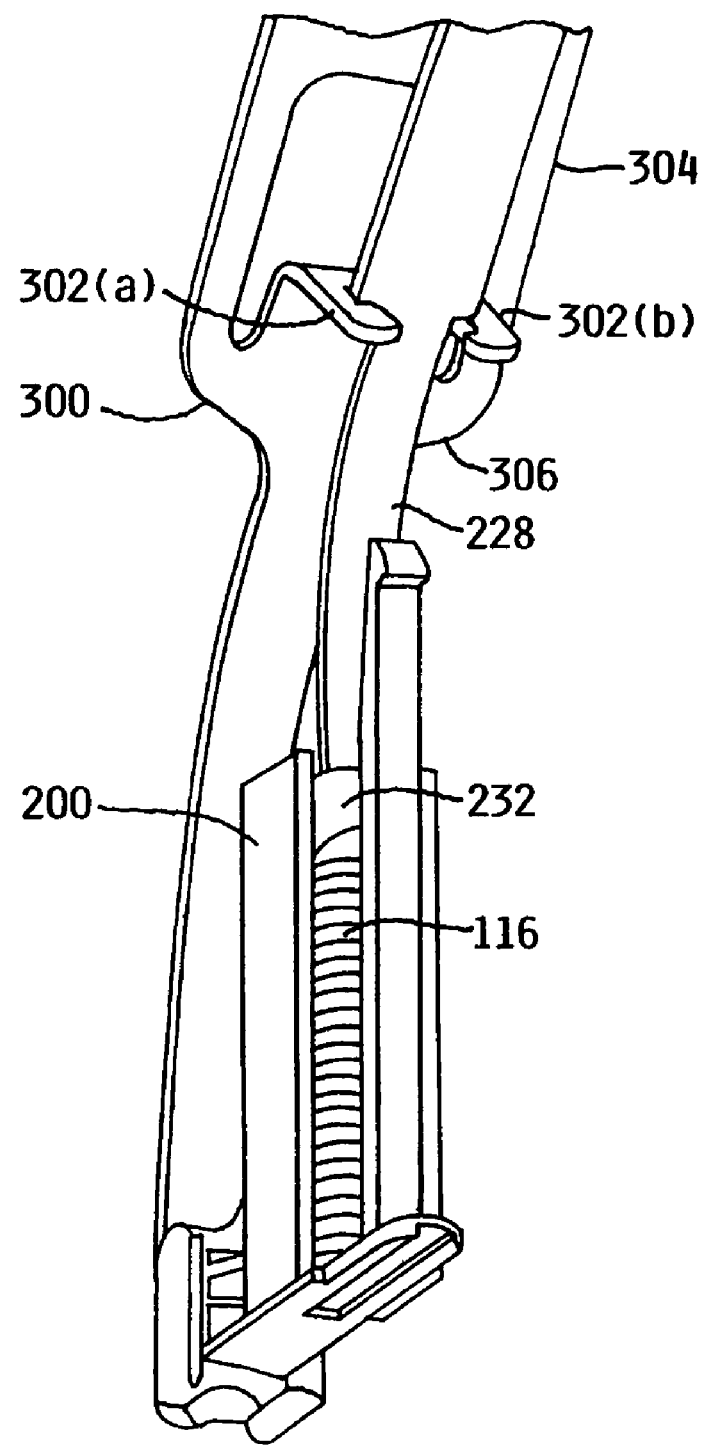
FIG. 9 shows a rear perspective view of the cartridge of the present invention.
Figure 10:
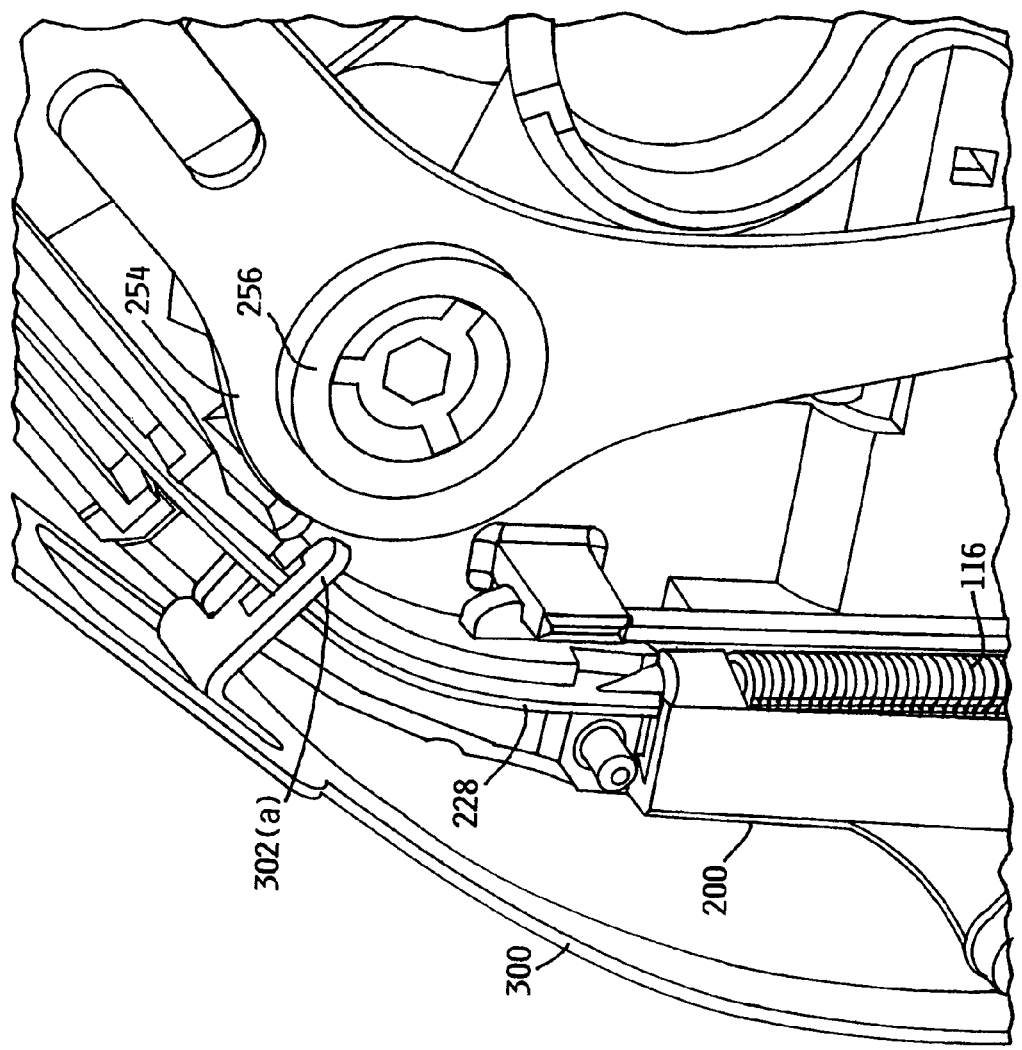
FIG. 10 shown an enlarged perspective view of a wound closure instrument incorporating the present invention.

A preferred embodiment of lock 300 will be described in more detail with respect to FIGS. 9-15. Lock 300 includes stopper arms 302(a), 302(b) that extend at approximately a 90 degree angle from lock 300, through an aperture in instrument 100. As shown in FIG. 9, rod 228 is disposed between stopper 302(a) and 302(b). Rod 228 is positioned at an angle approximately perpendicular to stopper 302(a) and 302(b). Rod 228 includes a wide section 304 near the end of the rod 228 adjacent to the biasing member 230. Rod 228 also includes a narrow section 306 between the wide section 304 and the plug 232. As shown in FIG. 9, the stopper 302 of lock 300 prevents the wide section 304 of rod 228 from passing through stopper 302(a) and 302(b). In a preferred embodiment, plug 232 is disposed at least partially in the cavity of cartridge 200 when the movement of rod 228 is secured by lock 300. This mechanism, by its nature, prevents the plurality of fasteners from escaping from the top entrance of the cavity.

Figure 11:
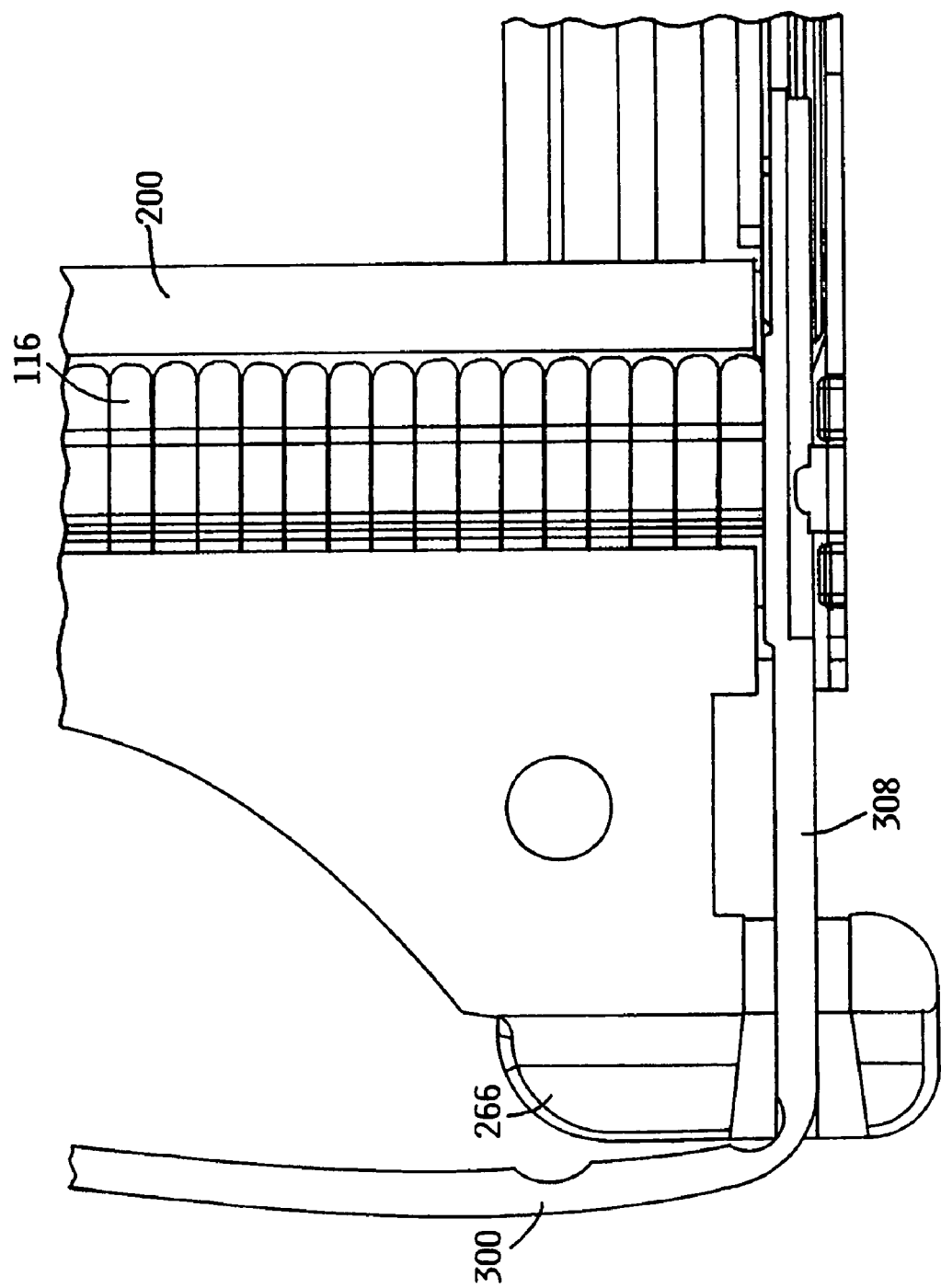
FIG. 11 is a side view of an instrument incorporating the present invention.
Figure 12:
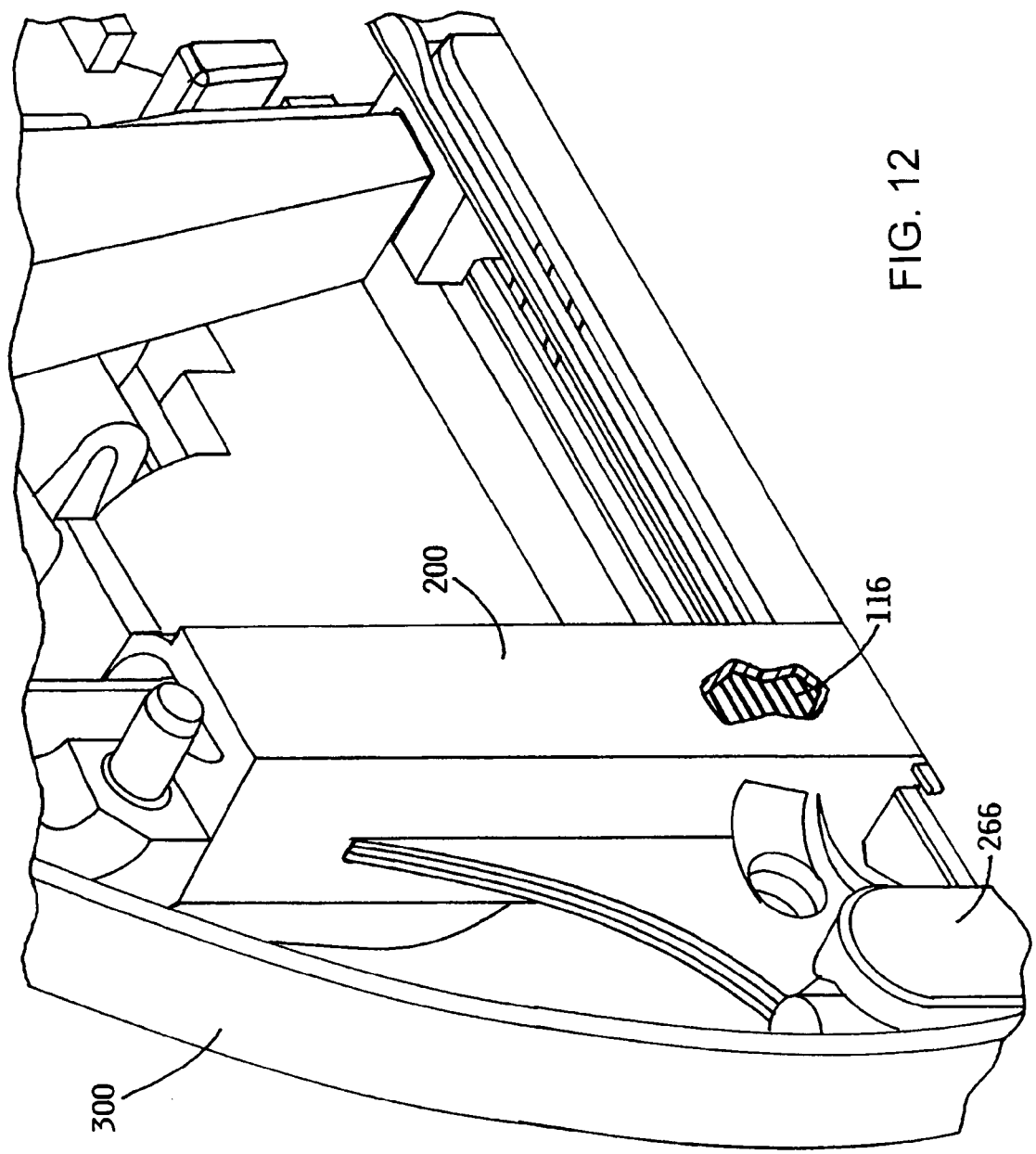
FIG. 12 is a partial front perspective view of an instrument incorporating the present invention.
Figure 13:
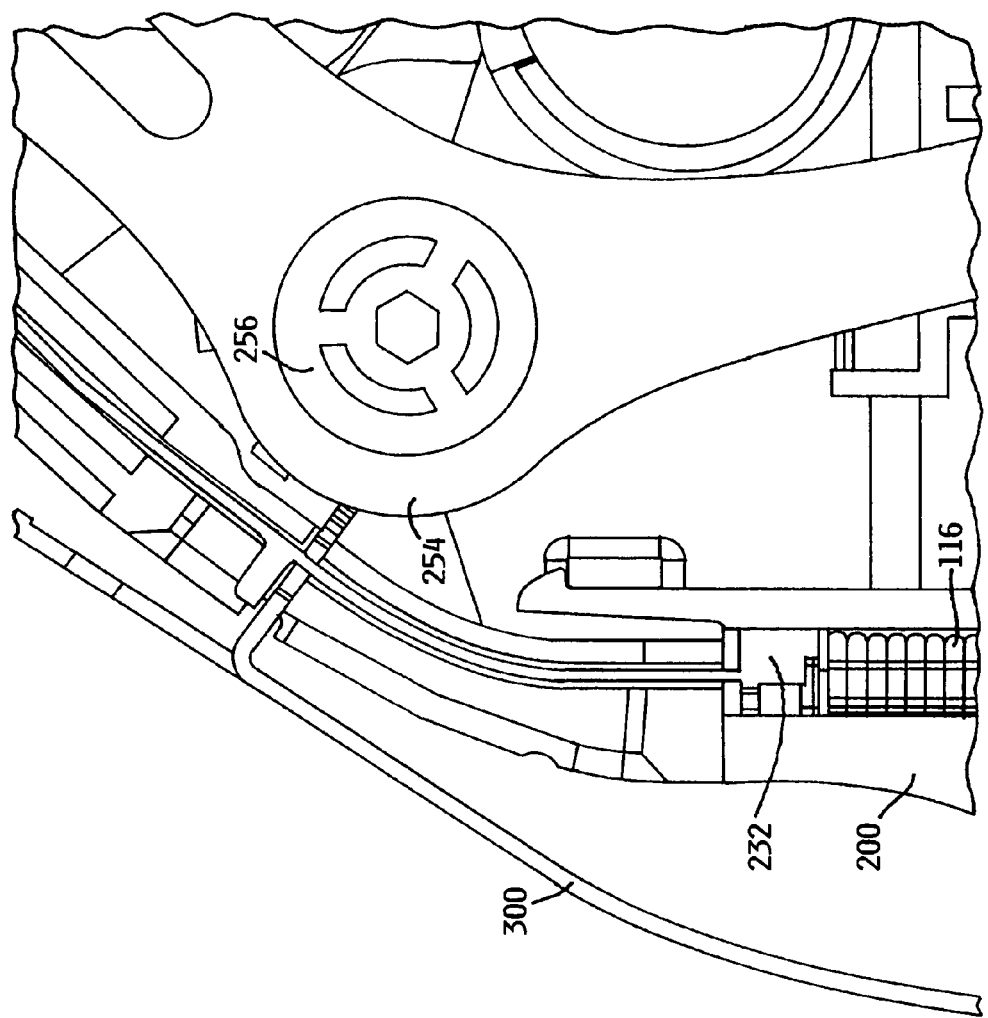
FIG. 13 is a side partial view of an instrument incorporating the present invention.
Figure 14:
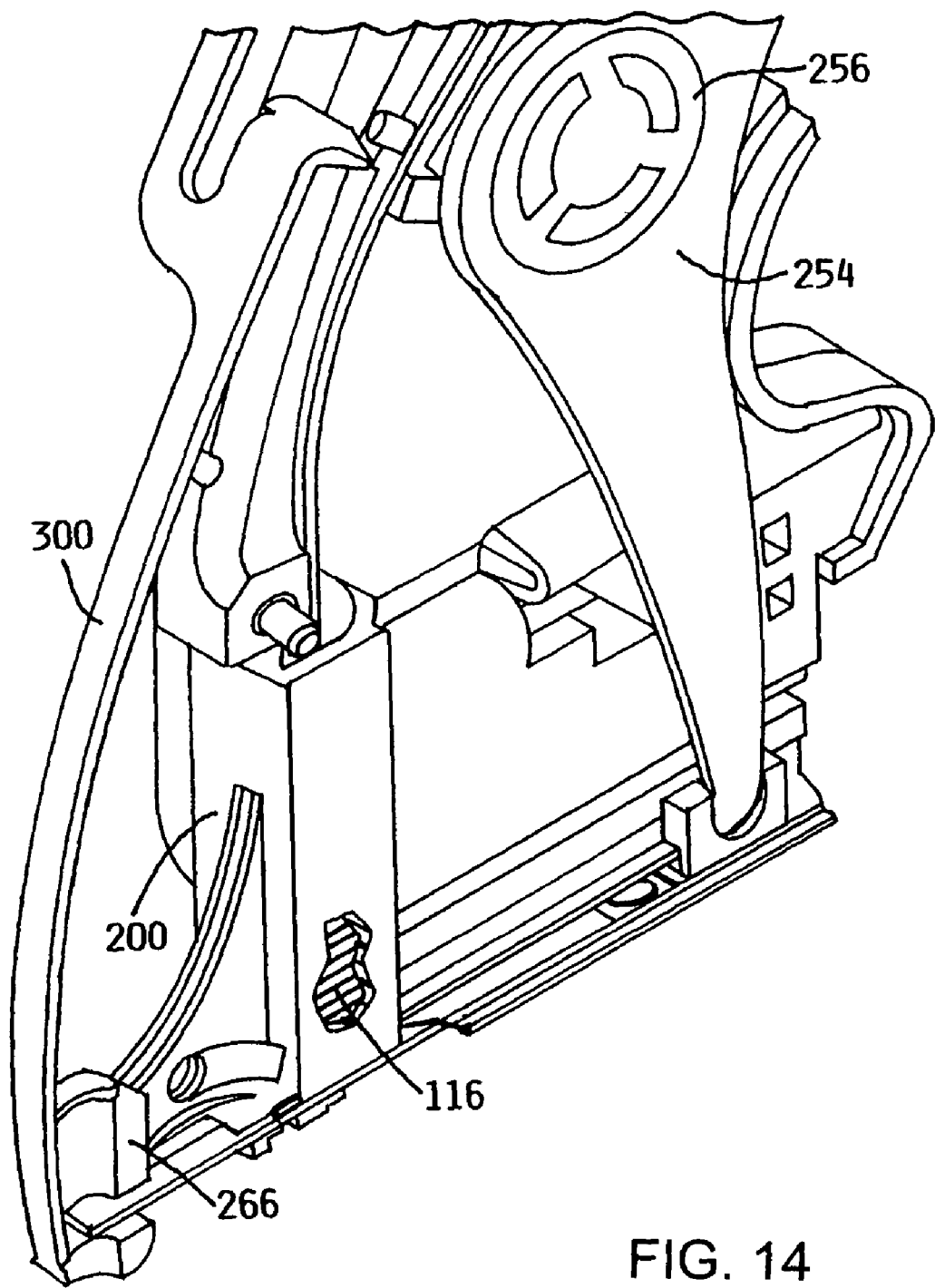
FIG. 14 is an enlarged cross-sectional perspective view of an instrument incorporating the present invention.
Figure 15:
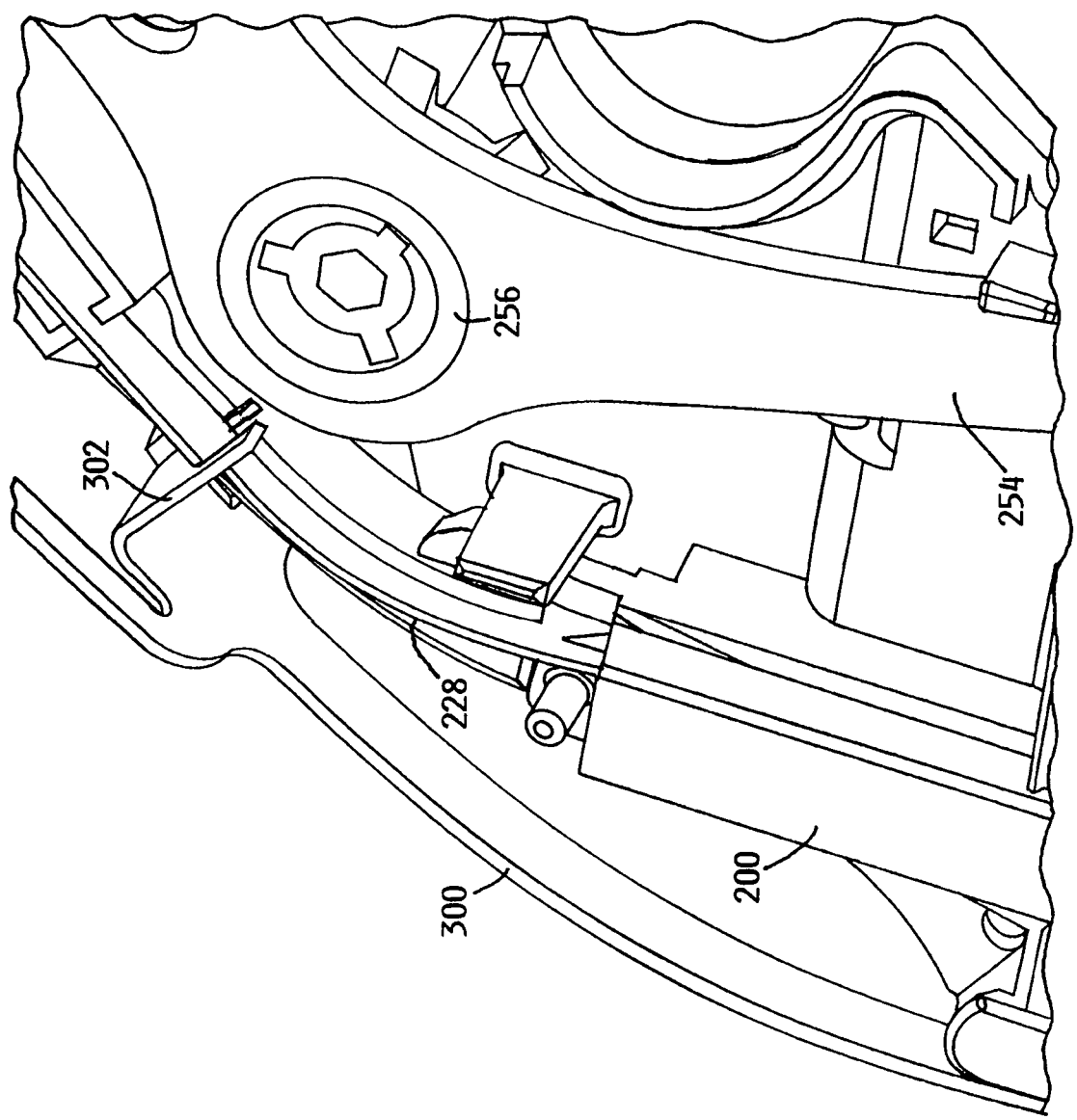
FIG. 15 is a partial perspective view of a wound closure instrument incorporating the present invention.

As shown in FIG. 11, lock 300 includes lower section 308 that extends into and through insertion head 266 and below cartridge 200. This feature of the invention holds the plurality of fasteners within the cartridge 200.

When instrument 100 is ready to be used, lock 300 is pulled away from instrument 100 such that lower section 308 slides out of insertion head 266. Stopper 302(a), 302(b) move away from rod 228 and enable rod 228 to slide downward due to the pressure of biasing member 230. The pressure of biasing member 230 enables plug 232 to apply pressure to the plurality of staples 116 so that the lowest staple is positioned against the applicator assembly 108. In this configuration, instrument 100 is ready for operation. Preferably, the biasing member 230 is a spring member. Alternatively, arrangements of elastic bands or belts, metal flat springs, or even a gas or liquid pressure activated mechanism could be used to provide the desired biasing force.

The advantages of the present invention are accomplished by an apparatus and method that engages skin tissue on each side of a skin opening with a fastener that is preferably made of a bioresorbable material. The fastener used may have a variety of configurations and be oriented in a variety of ways as will be further described herein. The location, geometry and orientation of the fastener and the dermal layers in relation to the mechanical apparatus of the present invention are all important considerations to obtaining the most optimal contact and compression of the dermal layer for efficacious closing of the opening. While the skin tissue has been described in connection with an opening in a single piece of tissue, it will be understood that the opening in the skin tissue could also be located between two separate and otherwise unconnected pieces of tissue, or even between a piece of tissue and a piece of biocompatible material to be secured to that piece of tissue.

Conventional sutures can act like a wick along which infection spreads throughout a wound. The present invention discloses a wound closure instrument 100 having a plurality of fasteners 116. The wound closure instrument 100 is particularly suitable when the length of the wound is substantially longer than the longitudinal length of a single fastener. This configuration allows for an interrupted closure having a single barb on each side of the wound. It also minimizes the chance of infection spreading from closure to closure. Moreover, the present invention allows for tissue closure without penetrating the epidermis. As a result, infection potential throughout the closure is both decreased and localized.

Research Findings for a Preferred Embodiment

A study was conducted to evaluate the clinical performance of absorbable subcuticular staples compared to metal skin staples in terms of safety, efficacy and cosmesis. The trial involved 15 gynecologic surgical patients. Observations of the incisions and patient impressions were documented at specified intervals for up to six weeks post-operatively. The absorbable staples demonstrated equivalent efficacy compared to metal skin staples with significantly improved cosmesis and patient satisfaction. A remarkable decrease in tissue irritation was found over the incisional areas closed with the absorbable staples compared to the regions closed with metal staples. Use of the subcuticular skin stapler was determined to be time effective. In addition, the absorbable staples eliminated the cost and patient discomfort associated with post-operative removal of metal staples.

The objectives of surgical wound closure are safe, effective wound healing with good cosmetic results. Effective time utilization of health care professionals in the surgical suite and post-operatively can be a determining factor in treatment. A number of incisional closure techniques are available, including a variety of suture materials, metal skin staplers, tissue glues and adhesive dressings. This study was conducted to compare this new modality to metal skin staplers which are routinely utilized in surgical practice.

Material and Methods

A single-fire metal applicator was trial to place Applicant's subcuticular absorbable staples (INSORB™ Subcuticular Skin Staple, Incisive Surgical, Inc., Plymouth, Minn.) in fifteen consecutive patients undergoing routine gynecologic surgeries with lower midline and Pfannenstiel incisions at Fairview Health System Hospitals (Minneapolis, Minn.).

The procedures included cesarean sections, abdominal hysterectomies, myomectomies and an ovarian cystectomy. Eight of the incisions were closed with a combination of metal skin staples and absorbable staples; seven of the incisions were closed entirely with the absorbable staples.

Figure 19:
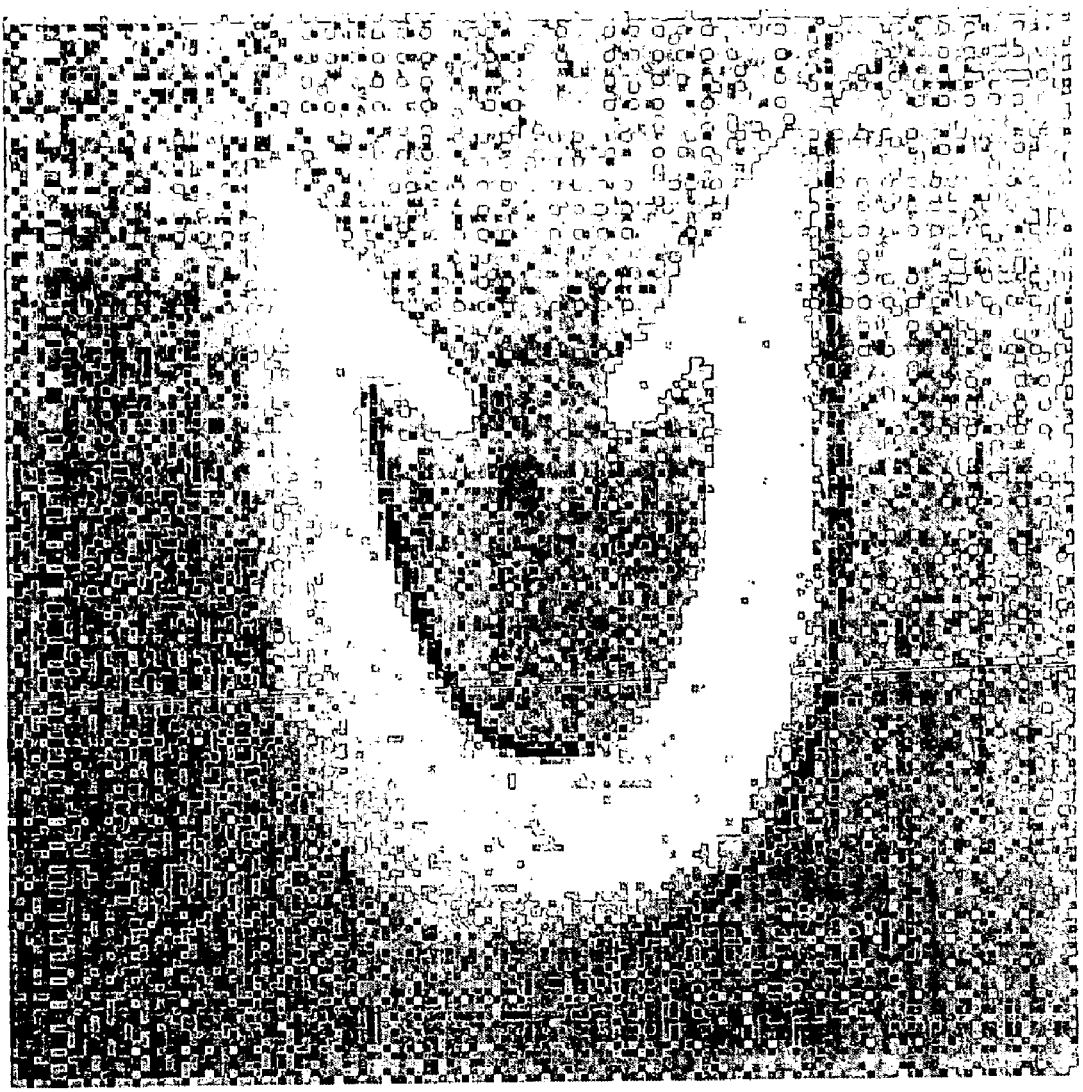
FIG. 19 is a top view of an absorbable subcuticular skin staple of the present invention.

The absorbable staples are made of a polylactidepolyglycolide co-polymer with an established history in wound closure. The staple design features a U-shaped curvature with cleats at the two distal ends as shown in FIG. 19.

In this study, Adson forceps in the form of a conventional single tweezer arrangement were used to sequentially grasp each side of the tissue wound and bring the tissue to the head of the fastening apparatus, thereby approximating the sides in a sequential manner, one side at a time. The tissue is held in place by tissue gatherers 246(a), 246(b), when the trigger assembly 104 of the stapler 100 is actuated. Placement of the staple is accomplished by advancing a staple carrier insertion slide 264 with sharp bilateral tips which deploys the staple forward, horizontally into the subcuticular tissue allowing the staple to capture a precise bite of dermis on each side of the incision with even approximation. The cleats of the staple hold the tissue in place after the staple carrier 264 is retracted. The absorbable staples were placed at approximately 8-10 mm intervals. Standard adhesive strips were used on the INSORB closure.

Results

The technique was found to successfully place absorbable subcuticular staples. It was also found to be intuitive and represent a relatively flat learning curve for the surgeon and surgical assistant. The device was determined to be time effective. The use of the absorbable subcuticular skin staples resulted in a very uniform, interrupted, everted skin closure without percutaneous tissue insult.

Incisional closures were observed and patient impressions documented at one, three and six weeks post-operatively.

The absorbable staples demonstrated equivalent efficacy compared to metal skin staples with significantly improved cosmesis and patient satisfaction. A remarkable decrease in tissue irritation over the incisional areas closed with absorbable staples was found compared to the regions closed with metal staples. The absorbable staples eliminated the cost and patient discomfort associated with post-operative removal of metal staples.

Documented patient impressions showed a significant increase in patient satisfaction with regards to comfort level and wound appearance. Patients overwhelmingly preferred the absorbable staple closure to the metal skin staple closure.

CONCLUSIONS

It has long been understood in the medical community that the optimal incisional closure technique results in minimal tension on the wound edges with good eversion and approximation. Use of the absorbable subcuticular skin staples results in a uniform, interrupted, everted skin closure without the percutaneous tissue insult associated with metal skin staples. The clinical results indicate that the incisional closure is equivalent to metal skin staples with respect to efficacy while additionally eliminating the cost and patient discomfort associated with removal of metal skin staples.

Applicant's early experience suggests that the use of absorbable subcuticular skin staples is significantly preferred by patients and is a reasonable alternative to metal skin staples.

Although the present invention has been described with respect to the various embodiments, it will be understood that numerous insubstantial changes in configuration, arrangement or appearance of the elements of the present invention can be made without departing from the intended scope of the present invention. Accordingly, it is intended that the scope of the present invention be determined by the claims as set forth.

What is claimed:

1. A device for gathering and securing opposed tissue with a fastener comprising:
   an applicator assembly operably configured to deploy a fastener having a generally symmetric u-shaped configuration in a first plane defined by a pair of tips and a body of the fastener, the applicator assembly including a head portion adapted to be positioned in an interface between opposed tissue;
   a tissue manipulation assembly operably configured to move from a relaxed position to a grasping position in a second plane generally transverse to the first plane; and
   a translating trigger assembly operably coupled to the applicator assembly and the tissue manipulation assembly, the trigger assembly operably configured to move from a relaxed position, through a first position, to a second position along a third plane that is generally transverse to both the first plane and the second plane,
   such that manual operation of the translating trigger assembly from the relaxed position through the first position along the third plane causes the tissue manipulation assembly to move in the second plane to gather at least portion of the opposed tissue, said opposed tissue being positioned on either side of the head portion without overlapping the opposed tissue along the third plane, and such that continued manual operation of the translating trigger assembly from the first position on to the second position along the third plane causes the applicator assembly to deploy the fastener into the opposed tissue along the first plane.

2. The device of claim 1, wherein the fastener is fabricated of a bioabsorbable polymer.

3. The device of claim 1, wherein the trigger assembly includes a plurality of connecting arms, wherein the movement of trigger assembly in the third plane from the relaxed position to the first position causes the connecting arms to rotate in the third plane and move the tissue manipulation assembly in the second plane from the relaxed position to the grasping position.

4. The device of claim 1, wherein the tissue manipulation assembly includes a tissue capture surface have a textured surface.

5. The device of claim 1, wherein the trigger assembly includes a rotatable member, wherein the movement of the trigger assembly in the third plane from the first position to the second position causes the rotatable member to rotate in the third plane to exert a force on the applicator assembly that deploys the fastener in the first plane in response thereto.

6. The device of claim 1, wherein the movement of trigger assembly from the relaxed position to the first position along the third plane defines an angle of less than 25 degrees.

7. The device of claim 6, wherein the movement of trigger assembly from the first position to the second position along the third plane defines an angle of less than 35 degrees.

8. The device of claim 1, wherein the applicator assembly is configured to deploy the fastener in less than 1 second.

9. The device of claim 1, wherein the trigger rotates about an axis that is generally parallel to the surface of the tissue.

10. A method for gathering and securing opposed tissue with a fastener comprising:
providing a fastener apparatus having:
an applicator assembly operably configured to deploy a fastener having a generally symmetric u-shaped configuration in a first plane defined through a widest aspect of the fastener;
a tissue manipulation assembly operably configured to move from a relaxed position to a grasping position in a second plane generally transverse to the first plane; and
a translating trigger assembly operably coupled to the applicator assembly and the tissue manipulation assembly, the trigger assembly operably configured to move from a relaxed position, through a first position, to a second position along a third plane that is generally transverse to both the first plane and the second plane;
positioning at least a portion of the applicator assembly in an interface between the opposed tissue;
advancing the trigger assembly from the relaxed position through the first position along the third plane wherein the tissue manipulation assembly moves in the second plane to gather a portion of the tissue; and
moving the trigger assembly from the first position to the second position along the third plane wherein the applicator assembly deploys the fastener into opposed tissue along the first plane.

11. The method of claim 10, wherein the step of moving the trigger assembly from the first position to the second position along the third plane deploys the fastener into subcutaneous tissue in a first direction without penetrating the epidermis of the tissue.

12. The method of claim 10, further comprising the step of releasing the trigger assembly, wherein the trigger assembly moves from a second position through the first position to a relaxed position in the third plane.

13. The method of claim 12, wherein the step of advancing the trigger assembly from the relaxed position through the first position to the second position occurs in less than one second.

14. The method of claim 12, wherein the step of releasing the trigger assembly causes the tissue manipulation assembly to move from a grasping position to a relaxed position.

15. The method of claim 14, where the step of releasing the trigger assembly loads the applicator with a second fastener.

16. The method of claim 10, wherein the method can be performed using a single hand.

17. A device for gathering and securing opposed tissue with a fastener comprising:
means for deploying a fastener having a generally symmetric u-shaped configuration in a first plane defined through a widest aspect of the fastener, the means for deploying the fastener is adapted to be position in an interface between opposed tissue;
means for capturing tissue in a second plane generally transverse to the first plane;
means for moving a trigger from a relaxed position, through a first position, to a second position along a third plane that is generally transverse to both the first plane and the second plane, such that movement of the trigger from the relaxed position through the first position along the third plane causes the means for capturing tissue to move in the second plane to capture at least portion of the opposed tissue, said opposed tissue being position on either side of the means for deploying the fastener without overlapping the opposed tissue along the third plane, and such that continued movement of the trigger means from the first position on to the second position along the third plane causes the device to deploy the fastener into the opposed tissue along the first plane.

18. A method for forming an interrupted closure of opposed tissue on adjacent sides of a skin wound comprising:
providing an apparatus having a plurality of fasteners, wherein the length of each of the plurality of fasteners is shorter than a longitudinal length of the skin wound;
positioning at least a portion of the fastener apparatus in an interface between the opposed tissue;
approximating the opposed tissue without overlapping the opposed tissue along the longitudinal length of the skin wound;
deploying a first fastener into subcutaneous tissue in a first direction along the longitudinal length of the skin wound without penetrating the epidermis of the tissue; and
deploying a second fastener into subcutaneous tissue in the first direction without penetrating the epidermis of the tissue such that an interrupted closure is formed whereby the plurality of fasteners are located discretely along the longitudinal length of the skin wound so as to prohibit communication of infectious material along the longitudinal length of the skin wound.

19. The method of claim 18, further comprising:
retaining said opposed tissue with a single barb located on each side of a fastener having a generally symmetric u-shaped configuration and wherein the barbs are deployed into and remain within the subcutaneous tissue of the opposite sides of the skin wound.

* * * * *

UNITED STATES PATENT AND TRADEMARK OFFICE
CERTIFICATE OF CORRECTION

PATENT NO. : 8,074,857 B2  
APPLICATION NO. : 11/022319  
DATED : December 13, 2011  
INVENTOR(S) : Peterson et al.

Page 1 of 1

It is certified that error appears in the above-identified patent and that said Letters Patent is hereby corrected as shown below:

Col. 3, line 26, insert --a-- after "least"

Col. 4, line 35, insert --of-- after "view"

Col. 6, line 9, delete "bottom-most" and insert --bottom most--

Col. 6, line 59, delete "kanted" and insert --canted--

Col. 6, line 62, delete "Kanted" and insert --Canted--

Col. 7, line 4, delete "kanted" and insert --canted--

Col. 7, line 23, delete "kanted" and insert --canted--

Col. 7, line 34, delete "kanted" and insert --canted--

Col. 9, line 22, delete "trial" and insert --trialed--

Col. 10, line 54, insert --a-- after "least"

Col. 11, line 5, delete "have" and insert --having--

Col. 12, line 14, delete "position" and insert --positioned--

Col. 12, line 24, insert --a-- after "least"

Col. 12, line 25, delete "position" and insert --positioned--

Signed and Sealed this  
Nineteenth Day of March, 2013

Teresa Stanek Rea  
*Acting Director of the United States Patent and Trademark Office*